(12) United States Patent
Yazdan Panah et al.

(10) Patent No.: US 12,371,646 B2
(45) Date of Patent: Jul. 29, 2025

(54) BIOREACTOR FOR RNA IN VITRO TRANSCRIPTION

(71) Applicants: CureVac Manufacturing GmbH, Tübingen (DE); Tesla Automation GmbH, Prüm (DE)

(72) Inventors: Benyamin Yazdan Panah, Tübingen (DE); Tilmann Roos, Tübingen (DE); Martin Kunze, Tübingen (DE); Felix Bertsch, Tübingen (DE); Aniela Wochner, Tübingen (DE); Michael Rauen, Tübingen (DE); Philipp Hoffmann, Tübingen (DE)

(73) Assignees: CureVac Manufacturing GmbH, Tübingen (DE); Tesla Automation GmbH, Prüm (DE)

( * ) Notice: Subject to any disclaimer, the term of this patent is extended or adjusted under 35 U.S.C. 154(b) by 1126 days.

(21) Appl. No.: 17/254,853

(22) PCT Filed: Jun. 28, 2019

(86) PCT No.: PCT/EP2019/067323
§ 371 (c)(1),
(2) Date: Dec. 21, 2020

(87) PCT Pub. No.: WO2020/002598
PCT Pub. Date: Jan. 2, 2020

(65) Prior Publication Data
US 2021/0261897 A1 Aug. 26, 2021

(30) Foreign Application Priority Data

Jun. 28, 2018 (WO) .................. PCT/EP2018/067504

(51) Int. Cl.
*C12M 1/06* (2006.01)
*B01F 33/451* (2022.01)
(Continued)

(52) U.S. Cl.
CPC .......... *C12M 21/18* (2013.01); *B01F 33/451* (2022.01); *B01F 35/5312* (2022.01);
(Continued)

(58) Field of Classification Search
CPC ...... C12M 21/18; C12M 27/02; C12M 41/48; B01F 33/451; B01F 35/5312; B01F 35/92;
(Continued)

(56) References Cited

U.S. PATENT DOCUMENTS 2,898,565 A * 8/1959 Fox ..................... H01F 27/245
336/5
5,149,195 A * 9/1992 Lofgren ................ B01F 27/111
366/265
(Continued)

FOREIGN PATENT DOCUMENTS

CN 106916743 7/2017
GB 2481425 12/2011
(Continued)

OTHER PUBLICATIONS

Murzabaev et al., "Handmade microfluidic device for biochemical applications in emulsion," *Journal of Bioscience and Bioengineering*, 121(4):471-476, 2016.
(Continued)

*Primary Examiner* — Liban M Hassan
(74) *Attorney, Agent, or Firm* — Parker Highlander PLLC

(57) ABSTRACT

The present invention relates to a bioreactor for RNA in vitro transcription, a method for RNA in vitro transcription, a module for transcribing DNA into RNA and an automated apparatus for RNA manufacturing. Further, the use of a bioreactor for RNA in vitro transcription as described herein is part of the present invention. The present invention relates to an RNA in vitro transcription reactor designed to be
(Continued)

operable in an automated manner under GMP-compliant conditions. In particular, said RNA in vitro transcription reactor allows repetitive use of DNA template for various RNA in vitro transcription reactions. Further, the invention relates to an apparatus for RNA manufacturing comprising (a) a module for template DNA synthesis, (b) a module for transcribing DNA into RNA comprising said RNA in vitro transcription reactor, and, optionally, (c) a module for RNA formulation.

13 Claims, 15 Drawing Sheets

(51) Int. Cl.
  *B01F 35/53*  (2022.01)
  *B01F 35/92*  (2022.01)
  *C12M 1/36*  (2006.01)
  *C12M 1/40*  (2006.01)
  *C12N 15/10*  (2006.01)
  *C12P 19/34*  (2006.01)
  *B01F 35/90*  (2022.01)
  *B01F 101/22*  (2022.01)

(52) U.S. Cl.
  CPC ............. *B01F 35/92* (2022.01); *C12M 27/02* (2013.01); *C12M 41/48* (2013.01); *C12N 15/1013* (2013.01); *C12P 19/34* (2013.01); *B01F 2035/98* (2022.01); *B01F 2035/99* (2022.01); *B01F 2101/22* (2022.01)

(58) Field of Classification Search
  CPC ............. B01F 2035/98; B01F 2035/99; B01F 2101/22; B01F 33/452; C12N 15/1013; C12P 19/34; C12Q 2521/119; C12Q 2563/143; C12Q 1/6865; C12Q 1/6895
  See application file for complete search history.

(56) References Cited

U.S. PATENT DOCUMENTS

| | | | | |
|---|---|---|---|---|
| 6,312,910 | B1 * | 11/2001 | Vellinger | C07K 1/24 436/526 |
| 6,361,749 | B1 * | 3/2002 | Terstappen | B03C 1/035 436/538 |
| 6,884,357 | B2 * | 4/2005 | Siddiqi | B03C 1/24 210/695 |
| 9,157,891 | B2 * | 10/2015 | Ovsyanko | G01N 27/745 |
| 10,837,039 | B2 * | 11/2020 | Wochner | C12M 41/48 |
| 2005/0032730 | A1 | 2/2005 | von der Mülbe et al. | |
| 2005/0059624 | A1 | 3/2005 | Hoerr et al. | |
| 2005/0250723 | A1 | 11/2005 | Hoerr et al. | |
| 2006/0013749 | A1 * | 1/2006 | Arencibia | B01F 27/91 422/202 |
| 2006/0188490 | A1 | 8/2006 | Hoerr et al. | |
| 2008/0025944 | A1 | 1/2008 | Hoerr et al. | |
| 2008/0267873 | A1 | 10/2008 | Hoerr et al. | |
| 2009/0311733 | A1 | 12/2009 | Korpela et al. | |
| 2009/0324584 | A1 | 12/2009 | Hoerr et al. | |
| 2010/0048883 | A1 | 2/2010 | Ketterer et al. | |
| 2010/0189729 | A1 | 7/2010 | Hoerr et al. | |
| 2010/0203076 | A1 | 8/2010 | Fotin-Mleczek et al. | |
| 2010/0264090 | A1 | 10/2010 | Ellis et al. | |
| 2010/0291156 | A1 | 11/2010 | Barner et al. | |
| 2010/0305196 | A1 | 12/2010 | Probst et al. | |
| 2011/0053829 | A1 | 3/2011 | Baumhof et al. | |
| 2011/0177592 | A1 * | 7/2011 | Faustman | B03C 1/288 435/325 |
| 2011/0250225 | A1 | 10/2011 | Fotin-Mleczek et al. | |
| 2012/0021043 | A1 | 1/2012 | Kramps et al. | |
| 2012/0258046 | A1 | 10/2012 | Mutzke | |
| 2013/0129754 | A1 | 5/2013 | Thess et al. | |
| 2013/0142818 | A1 | 6/2013 | Baumhof et al. | |
| 2013/0259879 | A1 | 10/2013 | Baumhof et al. | |
| 2013/0280283 | A1 | 10/2013 | Lorenz et al. | |
| 2013/0295043 | A1 | 11/2013 | Kallen et al. | |
| 2013/0336998 | A1 | 12/2013 | Kallen et al. | |
| 2015/0037326 | A1 | 2/2015 | Butler-Ransohoff et al. | |
| 2015/0050302 | A1 | 2/2015 | Thess | |
| 2015/0057340 | A1 | 2/2015 | Thess et al. | |
| 2015/0093413 | A1 | 4/2015 | Thess et al. | |
| 2015/0118183 | A1 | 4/2015 | Baumhof | |
| 2015/0118264 | A1 | 4/2015 | Baumhof et al. | |
| 2015/0165006 | A1 | 6/2015 | Thess et al. | |
| 2015/0184195 | A1 | 7/2015 | Thess et al. | |
| 2015/0218554 | A1 | 8/2015 | Thess | |
| 2015/0306249 | A1 | 10/2015 | Baumhof et al. | |
| 2015/0320847 | A1 | 11/2015 | Thess et al. | |
| 2016/0130345 | A1 | 5/2016 | Fotin-Mleczek et al. | |
| 2016/0166668 | A1 | 6/2016 | Kallen et al. | |
| 2016/0166678 | A1 | 6/2016 | Kallen et al. | |
| 2016/0166710 | A1 | 6/2016 | Baumhof | |
| 2016/0166711 | A1 | 6/2016 | Schnee et al. | |
| 2016/0168207 | A1 | 6/2016 | Kramps et al. | |
| 2016/0168227 | A1 | 6/2016 | Kallen et al. | |
| 2016/0235864 | A1 | 8/2016 | Schlake et al. | |
| 2016/0304883 | A1 | 10/2016 | Grund et al. | |
| 2016/0304938 | A1 | 10/2016 | Wochner | |
| 2016/0326575 | A1 | 11/2016 | von der Mülbe et al. | |
| 2016/0331844 | A1 | 11/2016 | Fotin-Mleczek et al. | |
| 2017/0014496 | A1 | 1/2017 | Fotin-Mleczek et al. | |
| 2017/0029847 | A1 | 2/2017 | Thess | |
| 2017/0114378 | A1 | 4/2017 | Wochner et al. | |
| 2017/0154713 | A1 * | 6/2017 | Simon | B23K 26/0006 |
| 2017/0252430 | A1 | 9/2017 | Fotin-Mleczek et al. | |
| 2017/0326225 | A1 | 11/2017 | Rauch et al. | |
| 2018/0044687 | A1 | 2/2018 | Thess et al. | |
| 2018/0125952 | A1 | 5/2018 | Fotin-Mleczek et al. | |
| 2018/0126003 | A1 | 5/2018 | Hoerr | |
| 2018/0142275 | A1 | 5/2018 | Roos et al. | |
| 2018/0147146 | A1 | 5/2018 | Eber et al. | |
| 2018/0148727 | A1 | 5/2018 | Grund et al. | |
| 2018/0201967 | A1 | 7/2018 | Eber et al. | |
| 2018/0208957 | A1 | 7/2018 | Roos et al. | |
| 2018/0214537 | A1 | 8/2018 | Mutzke et al. | |
| 2018/0237786 | A1 | 8/2018 | Schlake et al. | |
| 2018/0237817 | A1 | 8/2018 | Roos et al. | |
| 2018/0243219 | A1 | 8/2018 | Ketterer et al. | |
| 2018/0296663 | A1 | 10/2018 | Hipp et al. | |
| 2018/0298372 | A1 | 10/2018 | Funkner et al. | |
| 2018/0312545 | A1 | 11/2018 | Baumhof et al. | |
| 2018/0371392 | A1 | 12/2018 | Mayer et al. | |
| 2019/0010485 | A1 | 1/2019 | Yazdan Panah et al. | |
| 2019/0017100 | A1 | 1/2019 | Wochner et al. | |
| 2019/0024096 | A1 | 1/2019 | Schmid et al. | |
| 2019/0040378 | A1 | 2/2019 | Fotin-Mleczek et al. | |
| 2019/0049414 | A1 | 2/2019 | Wochner et al. | |
| 2019/0083602 | A1 | 3/2019 | Roos et al. | |
| 2019/0100784 | A1 | 4/2019 | Eber et al. | |
| 2019/0125857 | A1 | 5/2019 | Rauch et al. | |
| 2019/0133950 | A1 | 5/2019 | Eber et al. | |
| 2019/0160164 | A1 | 5/2019 | Rauch et al. | |
| 2019/0177714 | A1 | 6/2019 | Kunze et al. | |
| 2019/0185859 | A1 | 6/2019 | Fotin-Mleczek et al. | |
| 2019/0194760 | A1 | 6/2019 | Koch et al. | |
| 2019/0225971 | A1 | 7/2019 | Williams | |
| 2019/0241633 | A1 | 8/2019 | Fotin-Mleczek et al. | |
| 2019/0249219 | A1 | 8/2019 | Reichert et al. | |
| 2019/0336608 | A1 | 11/2019 | Baumhof et al. | |
| 2019/0336611 | A1 | 11/2019 | Baumhof et al. | |
| 2019/0343933 | A1 | 11/2019 | Horscroft et al. | |
| 2019/0343942 | A1 | 11/2019 | Fotin-Mleczek et al. | |
| 2019/0351044 | A1 | 11/2019 | Jasny et al. | |
| 2019/0351047 | A1 | 11/2019 | Jasny et al. | |
| 2019/0351048 | A1 | 11/2019 | Rauch | |
| 2019/0381180 | A1 | 12/2019 | Baumhof et al. | |
| 2020/0023076 | A1 | 1/2020 | Fotin-Mleczek et al. | |
| 2020/0085852 | A1 | 3/2020 | Fotin-Mleczek | |
| 2020/0085944 | A1 | 3/2020 | Heidenreich et al. | |
| 2020/0149026 | A1 | 5/2020 | Horscroft et al. | |
| 2020/0163878 | A1 | 5/2020 | Baumhof et al. | |

(56) References Cited

U.S. PATENT DOCUMENTS

| | | |
|---|---|---|
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0361761 A1 | 11/2021 | Lutz et al. |
| 2021/0379181 A1 | 12/2021 | Rauch et al. |
| 2021/0403925 A1 | 12/2021 | Chevessier-Tünnesen et al. |
| 2022/0040281 A1 | 2/2022 | Schwendt et al. |
| 2022/0073962 A1 | 3/2022 | Schwenger et al. |
| 2022/0133908 A1 | 5/2022 | Rejman et al. |
| 2022/0144877 A1 | 5/2022 | Heinz et al. |
| 2022/0211838 A1 | 7/2022 | Oostvogels et al. |
| 2022/0233568 A1 | 7/2022 | Schlake et al. |
| 2022/0296628 A1 | 9/2022 | Thess et al. |
| 2022/0313813 A1 | 10/2022 | Rauch et al. |
| 2022/0340641 A1 | 10/2022 | Aggarwal et al. |

FOREIGN PATENT DOCUMENTS

| | | |
|---|---|---|
| JP | 2009-517067 | 4/2009 |
| JP | 2010-527782 | 8/2010 |
| JP | 2017-085951 | 5/2017 |
| JP | 2018-057333 | 4/2018 |
| WO | WO 2004/015062 | 2/2004 |
| WO | WO 2013/171123 | 11/2013 |
| WO | WO 2016/062788 | 4/2016 |
| WO | WO 2018/211038 | 11/2018 |
| WO | WO 2021/123332 | 6/2021 |
| WO | WO 2021/254593 | 12/2021 |

OTHER PUBLICATIONS

PCT International Preliminary Report on Patentability issued in International Application No. PCT/EP2019/067323, issued Dec. 29, 2020.

PCT International Search Report and Written Opinion issued in International Application No. PCT/EP2019/067323, mailed Aug. 9, 2019.

* cited by examiner

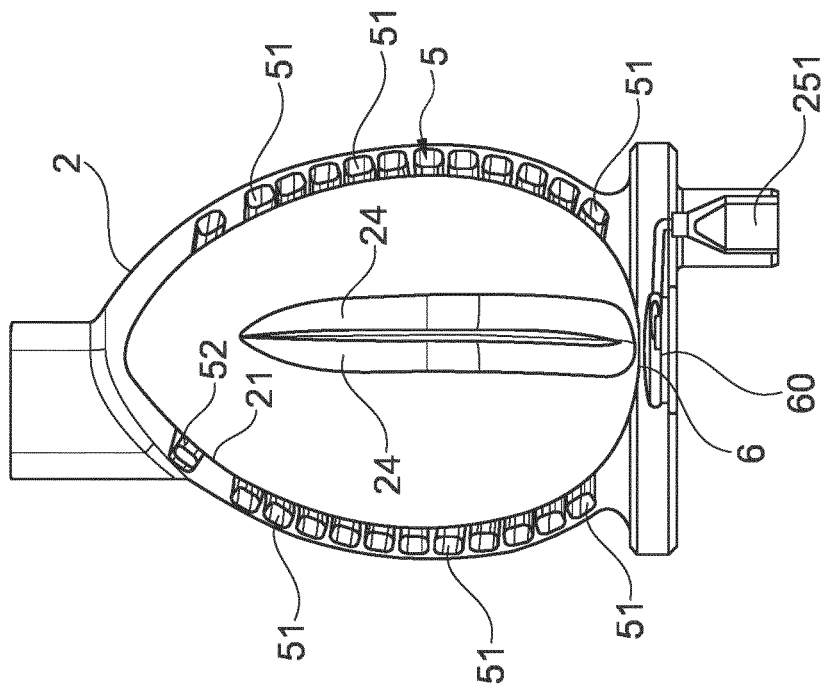
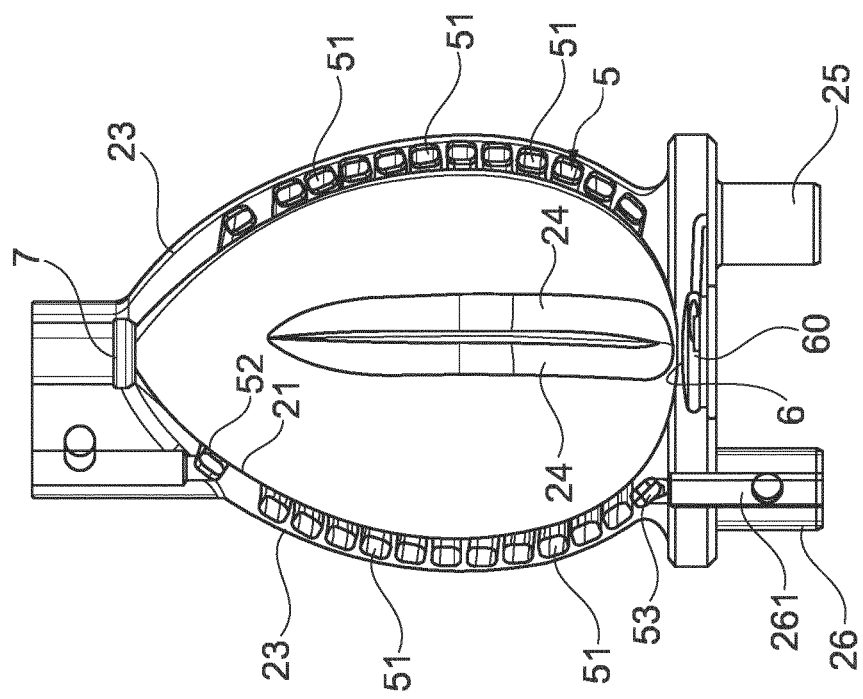

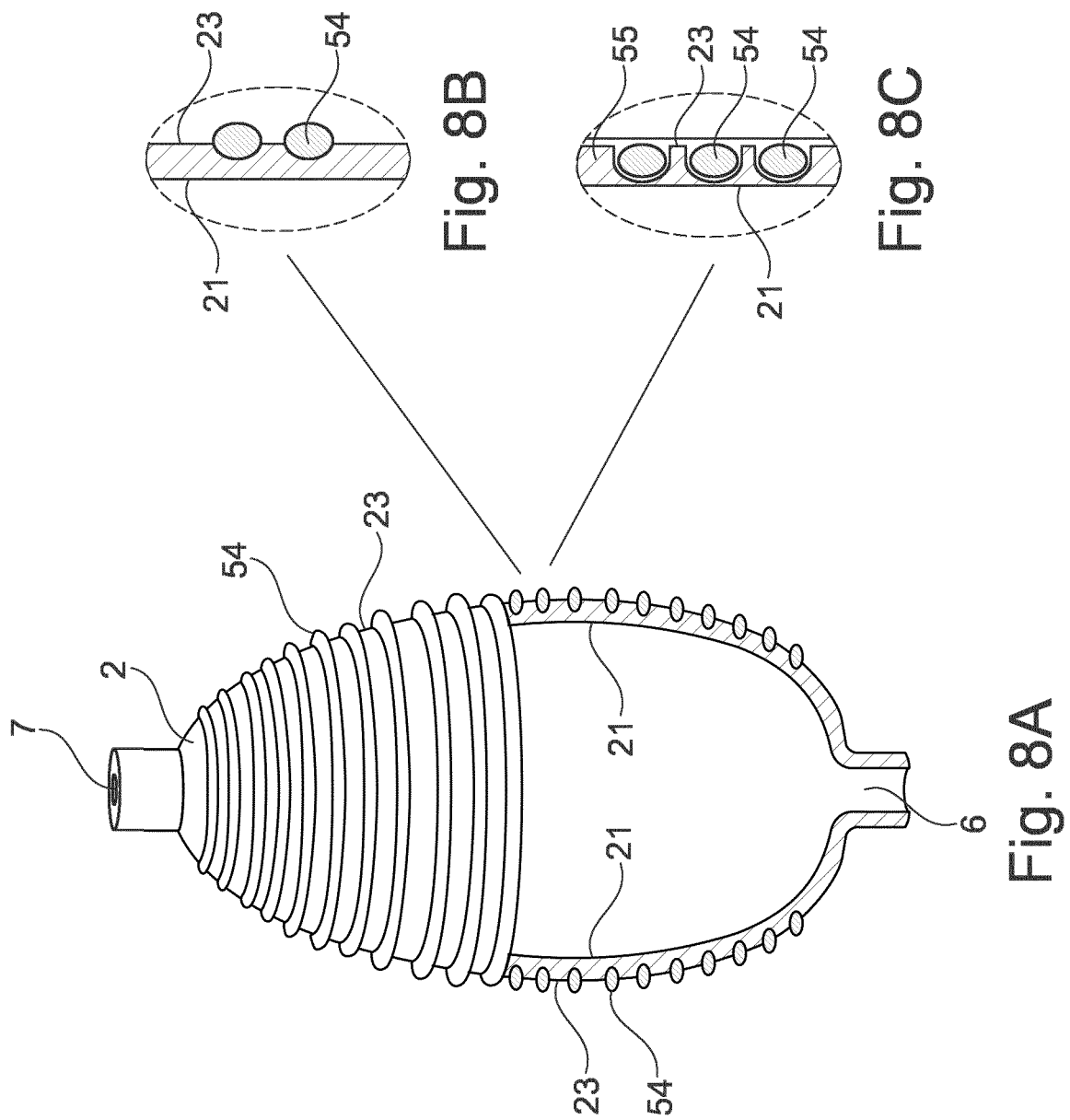

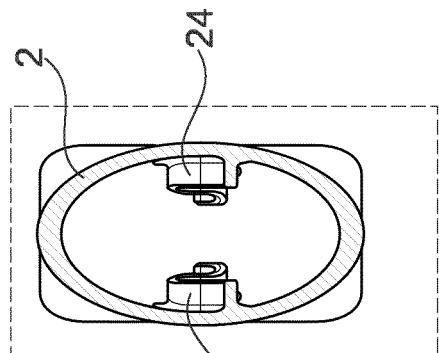
Fig. 9A
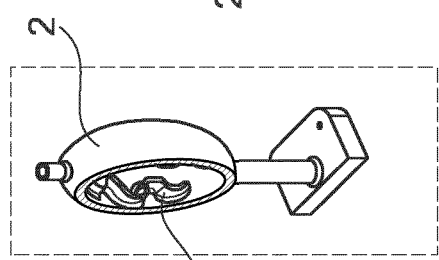
Fig. 9B
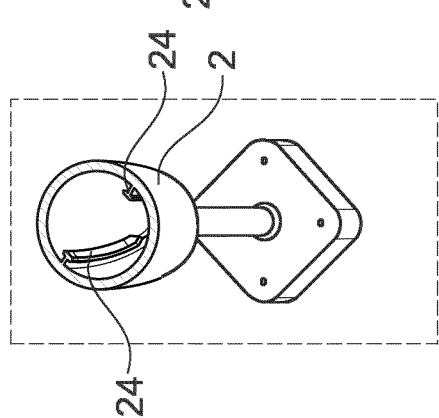
Fig. 9C
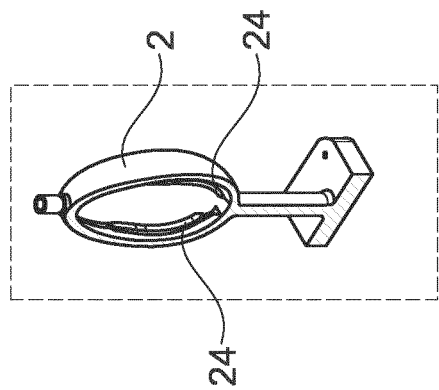
Fig. 9D
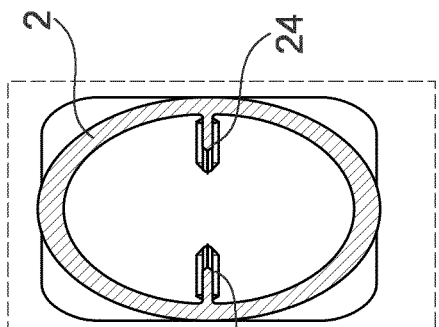
Fig. 9E
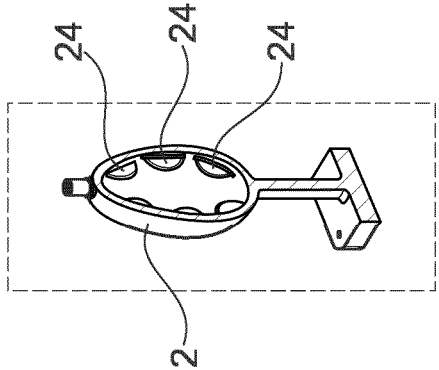
Fig. 9F
Fig. 9G
Fig. 9H

BIOREACTOR FOR RNA IN VITRO TRANSCRIPTION

The present application is a national phase application under 35 U.S.C. § 371 of International Application No. PCT/EP2019/067323, filed Jun. 28, 2019, which claims the priority benefit of International Application No. PCT/EP2018/067504, filed Jun. 28, 2018, the entire contents of each of which are hereby incorporated by reference.

FIELD OF THE INVENTION

The present invention relates to a bioreactor for RNA in vitro transcription, a method for RNA in vitro transcription, a module for transcribing DNA into RNA and an automated apparatus for RNA manufacturing. Further, the use of a bioreactor for RNA in vitro transcription as described herein is part of the present invention. The present invention relates to an RNA in vitro transcription reactor designed to be operable in an automated manner under GMP-compliant conditions. In particular, said RNA in vitro transcription reactor allows repetitive use of DNA template for various RNA in vitro transcription reactions. Further, the invention relates to an apparatus for RNA manufacturing comprising (a) a module for template DNA synthesis, (b) a module for transcribing DNA into RNA comprising said RNA in vitro transcription reactor, and, optionally, (c) a module for RNA formulation.

BACKGROUND OF THE INVENTION

Therapeutic nucleic acids including RNA molecules represent an emerging class of drugs. RNA-based therapeutics include mRNA molecules encoding antigens for use as vaccines (Fotin-Mleczek et al. 2012. J. Gene Med. 14 (6): 428-439). In addition, it is envisioned to use RNA molecules for replacement therapies, e.g. providing missing proteins such as growth factors or enzymes to patients (Karikó et al., 2012. Mol. Ther. 20 (5): 948-953; Kormann et al., 2012. Nat. Biotechnol. 29 (2): 154-157). Furthermore, the therapeutic use of noncoding immunostimulatory RNA molecules (e.g. WO2009/095226A2) and other noncoding RNAs such as microRNAs and long noncoding RNAs (Esteller, 2011. Nat. Rev. Genet. 12 (12): 861-74) or RNAs suitable for genome editing (e.g. CRISPR/Cas9 guide RNAs) is considered. Accordingly, RNA-based therapeutics with the use in immunotherapy, gene therapy and vaccination belong to the most promising and quickly developing therapeutic fields in modern medicine.

Currently established manufacturing processes for RNA molecules approved by regulatory authorities implement many separate manufacturing steps. Particularly, the respective manufacturing steps are performed by several different devices. Further, various separate quality controls are performed on DNA level and RNA level as described in detail in WO2016/180430A1.

A critical step in RNA production is the generation of a suitable DNA template, which at industrial scale is a major cost factor. Currently, DNA templates can only be used for a single RNA in vitro transcription reaction and need subsequently be destroyed by DNAse digestion and eventually removed by RNA purification in order to ensure efficacy and safety of the RNA-based therapeutics.

Manufacturing of RNA requires a large degree of manual handling in a GMP-regulated laboratory executed by well-trained technical staff. In consequence, current established manufacturing processes are time consuming, cost intensive, and require a lot of laboratory space and laboratory equipment.

SUMMARY OF THE INVENTION

As outlined above, there is the problem associated with common manufacturing devices and processes that RNA in vitro transcription currently requires a large degree of manual handling of well-trained technical staff. Thus, there is a need for providing an improved bioreactor for RNA in vitro transcription and an automated apparatus for RNA production to save time, space, equipment and personal.

An advantage of an improved bioreactor may be that it may allow for repetitive use of DNA templates in several RNA production processes which reduces the costs as less starting material (that is DNA template) has to be used and DNAse treatment can be omitted or substantially minimized. Moreover, an improved bioreactor may allow for the robust production of RNA with a higher purity profile (no residual DNAse, no residual DNA fragments in final RNA product). Advantages of an automated apparatus for RNA production are that the whole manufacturing process may be more robust and reliable (due to minimizing human error) and that the production of RNA may be accelerated.

Further, an acceleration of RNA manufacturing would be highly advantageous and of major importance for public health, especially in the context of pandemic scenarios. Further advantageous in that context would be the production of the RNA therapeutics in the region of the outbreak which would, however, require a portable RNA production apparatus.

The above problems are solved by the subject-matter of the independent claims, wherein further embodiments are incorporated in the dependent claims. It should be noted that the features of the invention described in the following apply equally to the bioreactor for RNA in vitro transcription, the method for RNA in vitro transcription, the module for transcribing DNA into RNA, the automated apparatus for RNA manufacturing and to the uses described herein.

In a first aspect, the present invention is directed to a bioreactor for RNA in vitro transcription comprising:
 a reaction vessel, and
 a magnet unit positioned at the reaction vessel.

The reaction vessel is suitable to hold at least one of magnetic particles, DNA templates, a DNA immobilization buffer, DNA magnetic particles and an RNA in vitro transcription (IVT) master mix. Thereby, the DNA magnetic particles are DNA templates immobilized on the free-floating magnetic particles. The magnet unit is configured to capture or to introduce a movement of the magnetic particles and the DNA magnetic particles hold in the reaction vessel. With such movement, a mixing or stirring of the magnetic particles and/or the DNA magnetic particles can be induced. Accordingly, depending on the number of additional components hold in the reaction vessel, a mixing or stirring of magnetic particles and/or DNA magnetic particles as well as at least one of DNA templates, a DNA immobilization buffer, and an IVT master mix can be induced by the magnetic unit. For instance, with DNA templates and free-floating magnetic particles as components hold in the reaction vessel, a mixing or stirring of the magnetic particles induced by the magnet unit may lead to mixed DNA magnetic particles, wherein the DNA magnetic particles are the DNA templates immobilised on the magnetic particles. In case the DNA magnetic particles and the IVT master mix are mixed or stirred due to a movement of the DNA magnetic particles induced by the magnetic unit, the thereby established more homogeneous mixture of DNA magnetic particles and the IVT master mix supports the RNA in vitro transcription of template DNA into RNA.

The bioreactor according to the present invention may further be suitable for a use under regulated conditions (GMP) suitable for pharmaceutical applications (e.g. pharmaceutical nucleic acid production). The bioreactor may allow a continuous production or repeated batch production of a liquid nucleic acid composition, preferably a ribonucleic acid (RNA) composition. In the context of the invention, the term RNA is used to indicate any type of ribonucleic acid. Accordingly, the term "RNA" may refer to a molecule or to a molecule species selected from the group consisting of long-chain RNA, coding RNA, non-coding RNA, single stranded RNA (ssRNA), double stranded RNA (dsRNA), linear RNA (linRNA), circular RNA (circRNA), messenger RNA (mRNA), RNA oligonucleotides, small interfering RNA (SIRNA), small hairpin RNA (shRNA), antisense RNA (asRNA), CRISPR/Cas9 guide RNAs, riboswitches, immunostimulating RNA (isRNA), ribozymes, aptamers, ribosomal RNA (rRNA), transfer RNA (tRNA), viral RNA (vRNA), retroviral RNA or replicon RNA, small nuclear RNA (snRNA), small nucleolar RNA (snoRNA), microRNA (miRNA), circular RNA (circRNA), and a Piwi-interacting RNA (piRNA).

In an embodiment, the inner surface of the reaction vessel has an ellipsoid or an oval inner geometry. It was found by the inventors, that an ellipsoid shape or oval inner geometry allows for a better mixing result. Additionally, such shapes allow for a better drip off or drain of fluids and may allow for better cleanability. The latter may prevent the formation of drops which otherwise could disadvantageously dry at the inner surface of the bioreactor. This may especially apply to e.g. proteinaceus residues of the fluid hold by the reaction vessel, which may e.g. harden or solidify at a temperature of 37° C. or higher.

In an embodiment, the inner surface of the reaction vessel has an egg-shape inner geometry. Such egg-shape may provide the same or improve the advantages as described above in context with the ellipsoid shape. An egg-shape may also provide for an optimal pressure distribution, optimal behaviour of the magnetic beads during mixing or steering, for holding the magnetic beads at the reaction vessel inner surface, distribution during cleaning process. An egg-shape may, for instance, be obtained from two half-spheroids with the same base radius, wherein one of the spheroids is a half-sphere with height equal to the base radius and the other spheroid has a height larger than the base radius. Alternatively, the inner surface of the reaction vessel may have a spheroidal-shape, in particular a shape of a sphere, or the inner surface may have a pill form. The inner surface of the reaction vessel may also have a form from a combination of an egg-shape and an ellipse or a combination of an egg-shape and a cylindrical shape. By such combination, one part of the inner surface of the reaction vessel has e.g. an egg-shape, while the remaining part of the inner surface has e.g. a cylindrical shape.

In an embodiment, the inner surface of the reaction vessel may have a spherical-shape inner geometry. Such spherical-shape may provide the same or improve the advantages as described above in context with the egg-shape reaction vessel.

In an embodiment, the inner surface of the reaction vessel has a shape without edges (e.g. a cuboid with rounded edges). This shape likewise supports an optimal drain of drops and thereby prevents hardening of proteinaceous residues of the fluid hold in the reaction vessel. Such a shape (no edges) allows for an effective cleaning procedure.

In an embodiment, the reaction vessel may have an inner surface without wide gaps or clefts. In that context, a gap or cleft larger than 2 μm, preferably a gap or cleft larger than 1 μm, more preferably a gap or cleft larger than 0.8 μm is still considered to be a "wide" gap or cleft. Such a shape (no wide gaps) allows for an effective cleaning procedure as larger gaps may provide a niche for microbial contamination and biofilms or residues.

In an embodiment, the movement of the magnetic particles and/or the DNA magnetic particles is configured such that a sedimentation of the particles hold in the reaction vessel is avoided. Additionally or alternatively, the movement of the magnetic particles and/or the DNA magnetic particles is configured to keep the particles comprised on the reaction vessel free-floating in such a way that a sedimentation at the reaction vessel's bottom can be prevented. Further, a mixing or swirling process is improved by keeping the particles in the vessel free-floating and/or that coagulation of beads is prevented or reduced. Advantageously, keeping magnetic particles and/or the DNA magnetic particles free floating and/or avoiding sedimentation of magnetic particles and/or the DNA magnetic particles improves biochemical reactions in the bioreactor, namely DNA immobilization and RNA in vitro transcription.

In an embodiment, the magnet unit of the bioreactor is given by an array of electromagnets. The latter may be positioned on or in proximity to the outer surface of the reaction vessel. Individual electromagnets out of the array may be individually switched on or off. In such a way a mixing or swirling of magnetic particles and/or DNA magnetic particles hold in the reaction vessel may be improved and better controlled. Said array of electromagnets is preferably not movable and the bioreactor itself is not movable (no shaking etc.) and mixing or swirling is introduced by a cooperation of magnetic particles and/or DNA magnetic particles and the magnet unit.

The magnet unit may alternatively, in another embodiment, be a permanent magnet or an electromagnet, which is movable in a longitudinal direction along a longitudinal axis of the reaction vessel. In addition or instead of such longitudinal movement, the permanent magnet or electromagnet may be movable in a transversal direction, towards and apart from the reaction vessel. Similarly to the case of an array of electromagnets, a longitudinally and/or transversally movable permanent or electromagnet may allow for a better control of mixing/swirling and a better mixing result.

The magnet unit may alternatively, in yet another embodiment, be given by an electromagnet and preferably by at least one induction coil. In this case, the magnet unit is movable in a longitudinal direction along a longitudinal axis of the reaction vessel. In addition, the magnet unit is rotatable around a vertical axis of the reaction vessel.

Suitably, the magnet unit may be arranged in form of at least one Helmholtz coil.

A position of the magnet unit in proximity of the reaction vessel refers to a distance between magnet unit and reaction vessel, which still allows for a suitable magnetic field to be established inside the reaction vessel when the magnet unit is turned on. Thereby, the strength and the form of the magnetic field have to be such that a swirling/mixing of magnetic particles may be induced and/or magnetic particles may be captured on the inner surfaces of the reaction vessel.

In an embodiment, the magnet unit is configured to rotate around a longitudinal axis of the reaction vessel, wherein a rotation direction of the magnet unit is switchable during mixing. The magnet unit may introduce a movement of the magnetic particles in a radial direction of the reaction vessel by inducing the magnetic particles in a radial direction relative to the longitudinal axis of the reaction vessel. The magnetic force can be static or dynamically generated by rotating the magnet unit around the reaction vessel to cause a rotation, accordingly mixing of the magnetic particles. Rotation direction of the magnet unit may be clockwise or anticlockwise relative to the longitudinal axis of the reaction vessel and/or alternately changed. Accordingly, the magnetic particles may stay free floating in a contactless manner, hence mixing of the components may be improved. As soon as the rotation of the magnet unit stops, the magnet particles (e.g. DNA magnetic particles) are captured at the inner surface of the reaction vessel and do not rotate any more. Accordingly, the magnet unit is configured to (i) rotate around a longitudinal axis of the reaction vessel to introduce a movement of the magnetic particles as explained above and configured to (ii) capture the magnetic particles when stopping rotation.

In an embodiment, the magnet unit comprises a magnetic ring, wherein the magnetic ring is designed to surround the reaction vessel. To facilitate assembling and rotating of the magnet unit around the reaction vessel, the magnet unit may be formed in a ring shape. In other words, the reaction vessel may be positioned in a centre of a ring-shaped magnet unit such that the magnet unit encircles the reaction vessel.

In an embodiment, the magnetic ring comprises at least a first rod and a second rod extending from an inner circumference of the magnetic ring to a centre of the magnetic ring, so that the free ends of the first and second rods face each other. In an embodiment, the free end of the first rod comprises a magnet with an N pole and the free end of the second rod comprises a magnet with an S pole.

The disc- or ring-shaped magnet unit may comprise a magnet arranged in a circumferential direction of the magnetic ring. The magnet may be arranged directly at and in contact with the magnetic ring or offset from the magnetic ring closer to the reaction vessel positioned in the centre of the magnet ring to reduce a gap between the magnet and the reaction vessel. To hold the magnet apart from the ring, a magnet holder connected to an inner surface and extending to the centre of the ring may be used. The magnet holder may be designed as a holding rod such that one end of the holding rod is attached to the inner circumference of the magnetic ring and the other end of the holding rod holds the magnet. The magnetic ring and the holding rods may be separately produced and attached to each other or manufactured as one piece, for example, by moulding.

To effectively induce a movement of the magnetic particles, the magnetic ring may comprise at least two rods spaced apart from each other along the circumference of the magnetic ring such that the free ends of the rods face each other. Further, to each free end of the rods a permanent magnet with an N pole and an S pole may be alternately attached. Accordingly, when rotating the magnetic ring, the magnetic particles may be rotatably induced around the reaction vessel, which causes an improved mixing of the components in the reaction vessel.

To effectively capture magnetic particles, rotation of the magnetic ring may be stopped after mixing the components in the reaction vessel.

In another embodiment, the magnetic ring comprises a plurality of rods, wherein the plurality of the rods extend from an inner circumference of the magnetic ring to a centre of the magnetic ring and are arranged in a star shape evenly spaced apart from each other. Preferably, a magnet with an N pole and a magnet with an S pole are arranged alternately at each free end of the rods.

In a preferred embodiment, the magnetic ring may comprise an even number of rods such that the plurality of rods, and accordingly the plurality of magnets attached to each free end of the rods are arranged in a paired manner to provide a heterogeneous or periodic magnet field. Further, the evenly along the circumference of the magnetic ring spaced rods allow a symmetric magnet field inducing the magnet particles inside the reaction vessel.

In an embodiment, the magnetic ring and the rods are configured to form a laminated stack for shielding periphery components from a magnet field. The magnetic ring and the rods may be made of a plurality of laminated electrical sheets, which are magnetisable. The laminated electrical sheet may comprise electrical steel and may be used for an electrical insulation. The laminated stack may screen the magnetic field generated by the permanent magnets attached to the free ends of the rods and influence no other devices besides the reaction vessel. Shielding of the magnetic field is particularly advantageous and allows the integration of the bioreactor in an apparatus comprising other devices/components that may be influenced by magnetic fields.

In an embodiment, the magnetic ring comprises a plurality of guide plates extending from an inner circumference of the magnetic ring to a centre of the magnetic ring. Preferably, each guide plate comprises an electric coil configured for generating a magnetic field. The magnetic ring may comprise at least one, preferably a plurality of electromagnets generating magnet fields by an electromagnetic coil. The guide plate may be arranged in a star shape along the circumference of the magnet ring and extend to the centre of the magnet ring where the reaction vessel may be positioned. The electromagnetic coils enable the magnetic field to be quickly changed by controlling the amount of electric current.

In an embodiment, the magnetic ring is arranged in a housing having cooling means. The cooling means may be integrated in the housing of the magnetic ring along the circumference of the magnetic ring to carry away heat caused by high currents passing through the electromagnetic coils. The cooling means may be a cooling channel in which a cooling medium such as water is circulated. The cooling means may preferably be integrated in magnetic rings comprising an electromagnetic coil. The cooling means may not be integrated in magnetic rings comprising permanent magnets (and not comprising an electromagnetic coil).

In an embodiment, the magnet unit further comprises a first driving means configured to rotate the magnetic ring around a longitudinal axis of the reaction vessel and a second driving means configured to move the magnetic ring in a vertical direction along the longitudinal axis of the reaction vessel. The magnetic ring may be held by a frame which moves in the longitudinal direction of the reaction vessel. Accordingly, the magnetic field may be provided and changed both in the longitudinal direction and the radial direction of the reaction vessel when the magnet ring rotates and moves vertically, which may lead to an even better homogeneous mixing of the components in the reaction vessel.

The driving means for rotating the magnetic ring and the driving means for moving the magnetic ring in the vertical direction may be provided separately. The first driving means for rotating the magnetic ring may be arranged directly to the magnetic ring and positioned above the reaction vessel, whereas the second driving means for vertically moving the magnetic ring may be connected to the magnetic ring via the frame fixedly holding the magnet ring and allowing the magnetic ring to move vertically.

In an embodiment, the reaction vessel is paramagnetic such that magnetic particles and DNA magnetic particles may be withhold on the inner reaction vessel wall by a cooperation of the paramagnetic vessel and the magnet unit positioned at the reaction vessel. Thereby, the whole reaction vessel may be paramagnetic, or the inner surface of the reaction vessel may be paramagnetic, e.g. by comprising a paramagnetic material or a magnetically conductive material. The term "magnetisable" denotes throughout the invention that the reaction vessel or its inner surface may be temporarily magnetized such that magnetic particles may be attracted and withhold at the reaction vessel wall. The magnetization of the reaction vessel or its inner surface may however be reversed, such that magnetic particles and DNA magnetic particles withhold at the reaction vessel wall may be released. It is therefore important that the material of the bioreactor and/or the inner surface of the bioreactor are not permanently magnetized by switching on the magnet unit (that is, not ferromagnetic).

Accordingly, in a preferred embodiment, the reaction vessel is paramagnetic. In other embodiments, the reaction vessel is configured to allow penetration of a magnetic field without being magnetisable.

In an embodiment, the magnet unit is configured to be periodically active to mix the magnetic particles and/or the DNA magnetic particles. A periodic activation of the magnet unit may lead to an improved mixing of the components as compared to a continuous activation of the magnet unit. Such periodic activation of the magnet unit leading to an improved mixing of the components has to be adjusted in a way to keep the magnetic particles or the DNA magnetic particles free floating, and to allow a mixing in such a way that biochemical reactions occur in an optimized manner (all components involved in the biochemical reaction, e.g. in the RNA in vitro transcription are mixed and get in contact to each other that RNA synthesis occurs). It is likewise important to adjust the mixing induced by the periodically active magnet and the DNA magnetic particles/magnet particles in a way that unwanted shear forces are minimized and that heat development is reduced (heat development may be induced by transformation of magnetic energy into heat, or induced by friction heat).

In an embodiment, the magnet unit is configured to be activated to capture the DNA magnetic particles between two or more subsequent RNA in vitro transcriptions on the same DNA templates (provided in form of DNA magnetic particles). Such capture may be associated with a magnetization of the reaction vessel which leads to withholding the DNA magnetic particles at the inner surface of the reaction vessel and/or may be associated with a magnetization of magnetisable but chemically inert beads or spheres within the reaction vessel Advantageously, such capture allows for a re-use of DNA magnetic particles in two or more RNA in vitro transcription reactions and thereby reduces time of production by decreasing template provision scale and costs of the RNA product (DNA template can be used several times).

In an embodiment, the magnet unit is configured to be activated to remove the magnetic particles and DNA magnetic particles. Such removal of magnetic particles and DNA magnetic particles may be intended for a cleaning of the reaction vessel. The removal of DNA magnetic particles may be performed after the last RNA in vitro transcription reaction (e.g. by pausing the rotation of the magnetic ring).

Such removal of DNA magnetic particle has the advantage that DNA can be removed without enzymatic digestion via e.g. DNAse which reduces DNA contaminations and enzyme contaminations in the final RNA product (no DNA digestion products, no DNAse enzyme), and reduces costs of the RNA product (no control for DNAse contamination in end-product needed, no DNAse enzyme needed).

In an embodiment, no mechanical motion introducing means for the magnetic particles and DNA magnetic particles are comprised. According to this embodiment, there are no additional mechanical stirrers or agitators which can induce a mixing or stirring of the components hold in the reaction vessel, so that the mixing is only induced by the magnet unit. This is particularly advantageous in the context of the invention as mechanical motion introducing means positioned inside the reaction vessel may cause the formation of unwanted precipitations (e.g. precipitations on the mechanical stirring means). Moreover, the absence of mechanical motion introducing means also improves the cleaning of the bioreactor (reduced surface, no edges inside the reaction vessel).

In an alternative embodiment, a mechanical motion introducing means for the magnetic particles and DNA magnetic particles are comprised in form of a shaker (e.g., orbital shaker), wherein the shaker is preferably positioned outside the reaction vessel.

In an embodiment, a mixing or stirring of the components hold in the reaction vessel may be introduced by a combination of (i) cooperation of the magnetic particles and a magnet unit, (i) mechanical motion introducing means, and/or (iii) directing a process gas or a process fluid into the reaction vessel.

In an embodiment, the reaction vessel comprises at least one flow breaker arranged at least partially along an inner surface of the reaction vessel in a longitudinal direction of the reaction vessel. The flow breaker may disturb a uniform flow of the components in the reaction vessel and thereby improves mixing. Moreover, the flow breaker may prevent sedimentation of the magnet particles when the magnet ring stops rotating and/or changes rotation direction. Accordingly, the flow breaker may be designed continuously without any groove, in particular in a horizontal direction perpendicular to a longitudinal direction of the reaction vessel, in which the magnetic particles may be accumulated.

The flow breaker may protrude from the inner surface of the reaction vessel in a radial direction of the reaction vessel and extend along a longitudinal direction of the reaction vessel. The flow breaker may continuously extend from a top portion to a bottom portion of the reaction vessel or comprise a plurality of elements arranged separately from each other along the longitudinal direction of the reaction vessel. Accordingly, the flow breaker may comprise a plurality of protrusions which are preferably spaced apart from each other.

In an embodiment, the reaction vessel comprises two flow breakers spaced apart from each other along the circumference of the reaction vessel. The reaction vessel may comprise at least one, exactly two or more flow breakers. The flow breakers are preferably evenly distributed along the inner surface of the reaction vessel in the radial direction of the reaction vessel to improve mixing and to prevent sedimentation of the magnetic particles.

In an embodiment, the flow breaker is rib-shaped and the rib-shaped flow breaker may preferably comprise a T- or L shaped cross section. The flow breaker protruding from the inner surface in direction to the centre of the reaction vessel may be formed in an arc shape along the curved inner surface of the reaction vessel and comprise a plurality of curvature radii along the ellipsoid inner geometry of the reaction vessel. A radial cross section of the flow breaker relative to the longitudinal axis of the reaction vessel may also vary. For instance, the radial cross section may be formed as a T-, L- or convex shape. A protrusion length of the radial cross section of the flow breaker may also vary along the inner surface from the top portion to the bottom portion of the reaction vessel. In an embodiment, the flow breaker is corrugated. The rib-shaped flow breaker may be also wave-shaped along the inner surface of the reaction vessel, which may prevent a sedimentation of the magnetic particles. A wave-shaped surface of a corrugated flow breaker may be aligned perpendicular to the inner surface of the reaction vessel.

In an embodiment, a temperature element is positioned between the inner surface and the outer surface of the reaction vessel for adjusting a temperature of the reaction vessel. In other words, the reaction vessel may comprises a thick wall made of a solid material allowing integration of the temperature element between the inner surface and the outer surface. Accordingly, a fast temperature adjustment regarding heating and cooling of the reaction vessel may be facilitated.

In an embodiment, the temperature element comprises a heat exchange channel at least partially helically surrounding the reaction vessel in a radial direction of the reaction vessel. The heat exchange channel may be integrated between the inner surface and the outer surface and adapted to adjust the temperature in the reaction vessel. To provide an effective and uniform heating or cooling, the heat exchange channel may completely surround the reaction vessel and a heat exchange medium may flow inside the heat exchange channel.

In an embodiment, the heat exchange channel comprises a first end and a second end, wherein the first end is arranged at a top portion of the reaction vessel and the second end is positioned at a bottom portion of the reaction vessel. The helically arranged heat exchange channel may have at least two ports for an inlet and/or an outlet of the heat exchange medium, wherein an efficient distribution of the heat exchange medium may be facilitated when one port is arranged at the top portion of the reaction vessel and the other port is arranged at the bottom portion of the reaction vessel, which may apply the gravitational force.

In an embodiment, the heat exchange channel and/or the reaction vessel is manufactured by means of an additive manufacturing process. Accordingly, a complex geometry of the reaction vessel including the heat exchange channel helically surrounding the reaction vessel between the inner surface and the outer surface of the reaction vessel may be easily realised.

In an embodiment, the reaction vessel further comprises a temperature element, which comprises a heating wire at least partially helically surrounding the reaction vessel in a radial direction relative to a longitudinal axis of the reaction vessel. As an alternative to the heat exchange channel, the heating wire may be arranged on the reaction vessel to adjust the temperature of the components in the reaction vessel. The heating wire may also helically surround the reaction vessel to provide uniform heating.

In an embodiment, the heating wire is at least partially integrated in an outer surface of the reaction vessel or at least partially coated on the outer surface of the reaction vessel. To minimize heat loss and to provide an efficient heating by the heating wire, the heating wire may be fixed to the outer surface of the reaction vessel. Alternatively or in addition to that, the outer surface of the reaction vessel may be coated with a heat isolation material and the heating wire may be at least partially retracted in the heat isolation material.

In an embodiment, the reaction vessel is dimensioned such that it can uptake at least 20 ml of fluid, or at least 50 ml of fluid, or at least 100 ml of fluid, or at least 500 ml of fluid. Preferably, it can uptake 20 ml to 100 ml or 20 ml to 50 ml of fluid. It may also be configured to uptake 50 ml to 100 ml of fluid. Of note, when used in a method as specified in the second aspect, said reaction vessel is filled to only about 60% to about 80% to allow sufficient shaking of the liquid. In a specific embodiment, the reaction vessel is dimensioned such that it can uptake about 100 ml of fluid, wherein only 60 ml to 80 ml of fluid is filled into the reaction vessel, corresponding to a reaction vessel filled to only about 60% to 80%. In another specific embodiment, the reaction vessel can uptake about 20 ml to 50 ml of fluid, wherein the reaction vessel shall be filled in this case to about 60%.

The IVT master mix may, according to an embodiment, comprise ribonucleoside triphosphates and DNA dependent RNA polymerase. The DNA immobilisation buffer may, according to an embodiment, comprise DNA and salt containing buffers. The DNA templates may be given by linear double stranded DNA templates, which are preferably PCR amplified DNA templates. In an embodiment, the magnetic particles may be given by magnetic beads, preferably streptavidin magnetic beads or chemically functionalized magnetic beads, most preferably paramagnetic streptavidin or chemically functionalized magnetic beads.

In an embodiment, the inner surface of the reaction vessel has a surface roughness value (Ra value) of Ra<=0.8, preferably Ra<=0.6. The inner surface may be, e.g., electropolished or otherwise, e.g. chemically or mechanically, treated such that the aforementioned Ra values are achieved. Such Ra values are particularly advantageous as such a material may improve the cleanability of the reactor because it may prevent or reduce deposition and hardening of e.g. proteinaceous residues or biofilms at the inner surface of the reaction vessel.

In an embodiment, the bioreactor comprises an inlet port, which allows for introducing a filling medium into the reaction vessel. Thereby, the inlet port is arranged below a maximal fluid amplitude or fluid level. In context of the present invention, a maximal fluid amplitude is understood to be the amplitude a fluid contained in the reaction vessel and brought into a shaking or rotational movement maximally reaches on the inner surface of the reaction vessel. In case of a rotational movement, centrifugal forces acting on the fluid molecules lead to a pushing of fluid upwards the inner surface of the reaction vessel. The boundary between moistened and dry area on the inner surface defines a line, which gives the maximal fluid amplitude. In other words, a maximal fluid amplitude can be associated with a line or area which is moistened in course of a shaking or rotational movement of fluid contained in the reaction vessel. A filling medium to be introduced through the inlet port of the reaction vessel may e.g. be given by magnetic particles, DNA templates, an immobilization buffer and/or an IVT master mix. Further filling media may be cleaning, wash and process fluids or the like. Positioning the inlet port below a maximal fluid amplitude prevents deposition and hardening of substances (e.g. proteins, DNA, or particles, or salts etc.) at the inner surface of the reaction vessel, which may for instance be the case for protein at temperatures around 37° C.

In an embodiment, the reaction vessel comprises a medium port at a bottom of the reaction vessel for supplying and/or removing medium into/out of the reaction vessel and the port is connectable to a valve means. In other words, the bioreactor comprises a combined inlet and outlet port (inlet/outlet port), preferably positioned at the lowermost point of the reaction vessel. The valve means may allow for introducing a filling medium into the reaction vessel and for draining the medium out of the reaction vessel. Advantageously, the valve means may be configured to keep e.g. the magnetic particles and DNA magnetic particles inside the reaction vessel when the valve means is closed, or to allow passage of e.g. fluids comprising RNA product when the valve means is open.

In an embodiment, the valve means comprises a magnetic trap. The latter is positioned at the medium port and configured to catch magnetic particles and DNA magnetic particles. In such a way magnetic particles and DNA magnetic particles may be caught when cleaning the reaction vessel. Additionally or alternatively, magnetic particles and DNA magnetic particles which unwantedly left the reaction vessel may be caught and thereby separated from e.g. produced RNA. The magnetic trap may be positioned outside the reaction vessel and may at least partially surround a medium pipe. The latter pipe may be connected to and downstream abuts the medium port of the reaction vessel. The medium port may be positioned at the lowermost point of the reaction vessel. In that way, fluids may easily outflow the reaction vessel driven by the gravitational force.

In an embodiment, the magnetic trap comprises magnetisable or magnetic spheres or magnetisable or magnetic rings and/or semi-permeable filters, which allow retaining magnetic particles and/or DNA magnetic particles. The magnetic trap may comprise an electromagnet or a permanent magnet. The magnetic trap may be controllable to prevent an escape of magnetic particles and or DNA magnetic particles from the reaction vessel. Such control can be advantageously used when separating produced RNA from magnetic particles and DNA magnetic particles.

In an embodiment, the bioreactor comprises a multi position valve. The latter is positioned downstream the magnetic trap and configured for directing a cleaning gas or a cleaning fluid through the port. This configuration serves to remove magnetic particles and DNA magnetic particles or other sedimentation collected at the port from the latter.

In an embodiment, the aforementioned multi position valve is configured to direct a process gas or a process fluid into the reaction vessel. The process gas or process fluid directed into the reaction vessel may lead to a mixing, stirring or swirling of the magnetic particles or DNA magnetic particles.

In an embodiment, the bioreactor comprises a valve means positioned at the outlet port, the inlet port, and/or the inlet/outlet port and is configured to keep e.g. the magnetic particles and DNA magnetic particles inside the reaction vessel when the valve means is closed, or to allow passage of e.g. fluids comprising RNA product when the valve means is open. Advantageously, the valve means may be configured to allow closing and opening of the outlet port and/or inlet port or the combined inlet/outlet port. Suitably, such a valve means may be a ball valve, a butterfly valve, a control valve, a diaphragm valve, a gate valve, a needle valve or a pinch valve or combinations thereof.

In an embodiment, the bioreactor comprises at least a first leg and a second leg vertically (along a longitudinal direction of the reaction vessel) supporting the bioreactor. The first leg comprises a first conduit and the second leg comprises a second conduit. The first conduit is configured to be in a fluid communication with the valve means and the second conduit is configured to be in a fluid communication with one end of the heat exchange channel of the temperature element. The first leg and the second leg may be positioned at the bottom portion of the reaction vessel and configured to vertically stabilise the reaction vessel. Moreover, the first and the second leg may comprise a conduit within the respective legs. The first end of the first conduit located in the first leg may be connected to the valve means to supply and/or drain the reaction components and the second end of the first conduit may be connected to a periphery device supplying and/or draining the reaction medium. Further, the first end of the second conduit located in the second leg may be connected to the second end of the heat exchange channel helically wound around the reaction vessel and the second end of the second conduit may be connected to a periphery device supplying and/or draining the heat exchange medium. Accordingly, the reaction vessel may be compactly designed.

In an embodiment, the bioreactor comprises an exit port. The exit port is connected to at least one of an exhaust duct and a waste channel. For instance, the exit port may be connected to at least both the exhaust duct and the waste channel by a multi position valve. The exit port may allow for receiving and venting exhaust gas or exhaust gases emerging within the reaction vessel. In case of waste fluid or a cleaning fluid, the exit port may serve for draining the fluid out of the reaction vessel. The exit port, the exhaust duct and/or the waste channel may hold at least one means for measuring and/or adjusting pressure.

In an embodiment, the bioreactor further comprises a Hall sensor. The latter is configured downstream the magnetic trap and serves to detect magnetic fields. The Hall sensor may watch or control that products, e.g. fluids, entering a capillary downstream the magnetic trap are free of magnetic particles and/or DNA magnetic particles. In this way, the Hall sensor helps to control the correct operation of the magnetic trap. As a consequence of a measurement of magnetic fields emerging from e.g. magnetic particles or DNA magnetic particles by the Hall sensor, a fault signal may be given.

In context of the present invention, "downstream" and "upstream" refer to a direction of motion of fluids or gases within the processes covered by the present invention. For instance, when a Hall sensor is configured downstream a magnetic trap, this implies that the magnetic trap and the Hall sensor are arranged at, e.g. surround, a capillary within which fluids or gases are conducted, and that a fluid or gas conducted within the capillary will first pass by the magnetic trap and afterwards pass by the Hall sensor.

In an embodiment, the reaction vessel comprises Titan. Titan comprises a lower remanence, in other words residual magnetism, which indicates a magnetization left behind in a ferromagnetic material after an external magnetic field is removed. Accordingly, the reaction vessel made of titan may provide an immediate interaction between the magnet force generated by the magnet ring and the magnet particles contained inside the reaction vessel.

Suitably, the reaction vessel has a material that is resistant to e.g. cleaning procedures (chemically resistant), extreme temperatures (e.g. 75° and 85° C. for cleaning procedure), extreme pH values (cleaning of the reactor with bases and acids, e.g. with NaOH), mechanical forces (e.g. frictions caused by magnetic particles), and/or corrosion. Moreover, materials of the reaction vessel should be temperature conductive at working temperatures around 20° C. (e.g. W/(mK) values of at least 10, preferably at least 15).

Suitably, and in the context of the invention of particular importance, the inner surface of the reaction vessel has a surface material that does not release unwanted compounds that may contaminate the end product. Suitable materials of the reaction vessel and/or the inner surface of the reaction vessel are austenitic stainless steel (e.g., 1.4404 (AISI 316L), 1.4435 (AISI 316L)), iron-less Hastelloy® alloys or titan (Ti1), which being paramagnetic, chemically resistant, pH resistant, temperature resistant, and temperature conductive.

Further suitable materials of the reaction vessel and/or the inner surface of the reaction vessel are glass (e.g. borosilicate glass), technical ceramics (e.g. FRIDURIT®), Polyaryletherketone (e.g., Polyetheretherketon (PEEK)), thermoplastics (e.g. DuraForm® Pa or DuraForm® GF), all of which being non-magnetizable, chemically resistant, pH resistant, and temperature resistant. An advantage of glass (e.g. borosilicate glass) may be that the reaction vessel may be inspected visually.

In an embodiment, the bioreactor further comprises a (semi permeable) filter element at the medium port or the medium pipe. The filter may help to withhold magnetic particles and DNA magnetic particles within the reaction vessel. The filter element may have a pore size smaller than 1 μm for an effective filtering. The semi-permeable filter may comprise a filter membrane with a molecular weight cutoff (MWCO) suitable for withholding magnetic particles and/or DNA magnetic particles. For preventing a clogging of the port by a clogged filter, the filter may preferably be a single use filter.

In an embodiment, the temperature element is configured to adjust the temperature within the reaction vessel to a DNA immobilization or RNA transcription temperature of 20° C. to 37° C. In addition, the temperature element may also be configured to adjust the temperature within the reaction vessel to a cleaning temperature of 75° C. to 85° C. The suitable temperature (e.g. 20° C. to 37° C. or 75° C. to 85° C.) may be controlled by at least one means for measuring and/or adjusting temperature (e.g. a temperature sensor), said at least one means may suitable be positioned at the inner surface of the reaction vessel and/or in proximity to the reaction vessel and/or in proximity to the temperature element. A temperature element and a means for measuring and/or adjusting temperature is particularly important as e.g. magnetic energy or friction may produce unwanted heat that may impede biochemical reactions (e.g. unwanted temperature increase in reaction).

In an embodiment, the bioreactor comprises an inlet flow cell and/or an outlet flow cell and/or an exit flow cell. The inlet flow cell may be arranged upstream the inlet port and the outlet flow cell may be arranged downstream the outlet port and the exit flow cell may be arranged downstream the exit port. The inlet flow cell and/or the outlet flow cell and/or the exit flow cell may be calibratable and may be arranged for monitoring a flow rate of fluids or gases flowing into or out of the reaction vessel. The latter may contribute to a partial control of the processes of e.g. RNA transcription or cleaning of the bioreactor in context of the present invention.

In an embodiment, the reaction vessel is configured to additionally hold at least one of the following elements given by a buffer suitable for RNA in vitro transcription, ribonucleoside triphosphates, a cap analogue, modified ribonucleoside triphosphates, a ribonuclease inhibitor, a pyrophosphatase, MgCl2, an antioxidant, a polyamine and a solution for cleaning and/or sanitizing.

In an embodiment, the reaction vessel may be further configured to hold at least one means for measuring and/or adjusting pH or concentration of contained components, as well as a magnesium concentration, phosphate concentration, temperature, pressure, flow velocity, RNA concentration and/or ribonucleotide triphosphate concentration. The means may be given by a respective sensors or a respective probe. Such mean or means may contribute to a monitoring of the processes covered by the present invention. The measuring means may be a measuring device or sensor and the adjusting means maybe be a dosage device. For instance, the means may be a sensor for measuring the pH of components contained in the reaction vessel, or a sensor for measuring the magnesium or salt concentration. Further, exemplarily, the means may be a device for measuring the temperature, pressure or flow velocity. In the latter case, the means may be, for instance, a flow-cell inside or at an outflow of the reaction vessel.

In an embodiment, the bioreactor is designed to operate in batch, a repeated batch, continuous mode or in a semi-continuous or continuous mode. Repeated batch RNA in vitro transcription (IVT) is preferred as it allows several reactions on the same DNA template with the advantages as already outlined herein.

In an embodiment wherein the bioreactor comprises mechanical motion introducing means, the bioreactor may comprise rotation means for rotating the reaction vessel. Such rotation may help to prevent a sedimentation of magnetic particles and DNA magnetic particles at the outlet port.

In a second aspect, the present invention is directed to a method for RNA in vitro transcription. The method comprises the following steps:
  providing DNA magnetic particles and IVT master mix in a reaction vessel of a bioreactor, wherein the bioreactor is designed according to at least one of the above described embodiments of the first aspect (S3a),
  mixing free-floating DNA magnetic particles with the IVT master mix by means of a cooperation of the DNA magnetic particles and the magnet unit of the bioreactor and/or by means of a shaker. To this end, the magnet unit may be configured to induce a movement of the DNA magnetic particles and the components of the IVT master by appropriate electromagnetic fields. As a result of the mixing, in vitro transcribed RNA is obtained (S3b).

The method of the second aspect may additionally comprise the following steps:
  providing magnetic particles, DNA templates, a DNA immobilization buffer in a reaction vessel of a bioreactor wherein the bioreactor is designed according to at least one of the above described embodiments of the first aspect (S1),
  mixing the magnetic particles, the DNA templates and the DNA immobilization buffer. Mixing is performed by means of a cooperation of the magnetic particles and a magnet unit and/or by means of a shaker (S2). To this end, the magnet unit may be configured to induce a movement of the magnetic particles and DNA magnetic particles by appropriate electromagnetic fields. As a result of the mixing, DNA magnetic particles, which are the DNA templates immobilized on the free-floating magnetic particles, are obtained. Said DNA templates immobilized on the free-floating magnetic particles may be mixed with IVT master mix to obtain RNA (as described above; S3). Accordingly, steps S1 and S2 are performed prior to the step S3.

The method of the second aspect may additionally comprise the following steps:

capturing DNA magnetic particles by means of the magnet unit and collecting/harvesting obtained in vitro transcribed RNA e.g. through the outlet port (S4a), providing fresh IVT master mix in a reaction vessel of a bioreactor of the first aspect (S4b), releasing captured DNA magnetic particles to provide free-floating DNA magnetic particles (S4c), mixing the free-floating DNA magnetic particles with the IVT master mix by means of a cooperation of the DNA magnetic particles and the magnet unit and/or by means of a shaker to obtain RNA (S4d).

Preferably, steps S4a-S4d are performed after step S3. Said method steps (S4) are particularly suitable in embodiments where more than one RNA in vitro transcription reaction is performed.

Preferably, said method steps are performed at least 2 times, e.g. 2, 3, 4, 5, 6, 7, 8, 9, 10 or up to 30 times.

In an embodiment, the method according to the present invention may further comprise the step of adjusting the pH and/or salt concentration.

In an embodiment, the method according to the present invention further comprises the step of tempering the reaction vessel to a temperature between 20° C. and 37° C. Such temperature may be suitable for RNA in vitro transcription. The tempering may be performed before filling the reaction vessel.

The reaction vessel may be tempered to a temperature between 20° and 25° C., preferably 22° C., in an additional method step for immobilisation of DNA templates on magnetic particles. Further, in an additional method step, the reaction vessel may be tempered to a temperature between 75° and 85° C. for/during a cleaning process of the reaction vessel.

In an embodiment, the method further comprises the step of cleaning the reaction vessel by a cleaning gas and/or cleaning fluid. Before or during cleaning, the reaction vessel may e.g. heated to an aforementioned temperature between 75° and 85° C. After obtaining the in vitro transcribed RNA, DNA magnetic particles may be removed by means of a cooperation of the DNA magnetic particles and the magnet unit. This method step allows removal of the DNA template without e.g. performing DNAse digestion.

To allow mixing or capturing/releasing of magnetic particles or DNA magnetic particles it is important that the magnetic particles are paramagnetic to avoid irreversible attachment to the wall of the reactor vessel during e.g. the mixing introduced by the magnet unit. Examples of suitable magnetic particles are Dynabead® magnetic beads (ThermoFisher Scientific).

The method may further comprise different quality control steps that may allow for assessment of e.g. RNA identity, RNA integrity, RNA purity etc. Said quality controls may be implemented in-line or at-line.

The method for RNA in vitro transcription as outlined herein may be performed on one DNA template to generate a RNA composition comprising one RNA species. In other embodiments, the method for RNA in vitro transcription may be performed on at least two different DNA templates to generate a composition comprising at least two RNA species. E.g., methods described in WO2017/1090134A1 may be adapted accordingly and performed in a reaction vessel of a bioreactor of the first aspect.

The method may further comprise a step of enzymatic RNA capping that may be performed in a reaction vessel of a bioreactor of the first aspect (e.g. using immobilized capping enzymes on magnetic particles; immobilized capping enzymes may be obtained using methods disclosed in WO2016/193226). The magnet unit may be configured to induce a movement of the capping enzymes on magnetic particles and the RNA by appropriate electromagnetic fields. As a result of the mixing, capped RNA is obtained.

The method may further comprise a step of enzymatic RNA Polyadenylation that may be performed in a reaction vessel of a bioreactor of the first aspect (e.g. using immobilized PolyA polymerases on magnetic beads immobilized PolyA polymerases may be obtained using methods disclosed in WO2016/174271). The magnet unit may be configured to induce a movement of the PolyA polymerases on magnetic particles and the RNA by appropriate electromagnetic fields. As a result of the mixing, polyadenylated RNA is obtained.

In a third aspect, the present invention is directed to a use of a bioreactor as described above in a method as described above.

Further, the bioreactor of the first aspect may be used for RNA in vitro transcription reactions where the DNA is free or immobilized on non-magnetic particles (e.g. agarose beads, sepharose beads, non-magnetic polystyrol beads, and other appropriate synthetic resins) and the mixing is introduced by means of a cooperation of magnetic particles that do not carry DNA template and the magnet unit of the bioreactor of the first aspect. In such an embodiment, the RNA in vitro transcription reaction can only performed once. Further, the bioreactor may be used in any enzymatic method involving nucleic acids (e.g., Polymerase Chain Reaction (PCR), isothermal DNA amplification, Reverse transcription of RNA into cDNA) wherein mixing is introduced by means of a cooperation of magnetic particles and the magnetic unit of the bioreactor of the first aspect.

In a fourth aspect, the present invention is directed to a module for transcribing template DNA into RNA. The module comprises a bioreactor according to at least one of the above embodiments of the first aspect, and further at least one of a unit for preparing an IVT master mix, a unit for preparing an immobilization buffer, a device for purifying an obtained RNA product, a device for RNA conditioning and/or a device for RNA sterile filtration.

In preferred embodiments, the device for purifying an obtained RNA product comprises an HPLC unit, preferably a unit for performing RP-HPLC. Particularly preferred in that context is RP-HPLC using a method disclosed in WO2008/077592 preferably using a porous, non-alkylated poly(stryrene-divinylbenzene) reverse phase, wherein the reverse phase is formed by beads or occurs as a polymerized block (e.g. monolithic). Alternatively, or in addition, the device for purifying an obtained RNA product may comprise an oligo dT purification unit for affinity purification of obtained polyadenylated RNA via oligo dT functionalized matrices or beads or columns (e.g. as described in WO2014152031A1).

In preferred embodiments, the device for RNA conditioning comprises a tangential-flow filtration unit. Particularly preferred in that context is tangential flow filtration as described in WO2016/193206, wherein TFF is used for diafiltration and/or concentration and/or purification of RNA.

In an embodiment, the module further comprises a media supply unit. The latter unit is configured to supply components of the IVT master mix to the unit for preparing the IVT master mix.

In an embodiment, the DNA template is an end-modified or end-functionalised PCR-generated DNA template. Preferably, the DNA template is a biotinylated PCR-generated DNA template, a non-modified or end-modified linearized plasmid DNA or a non-modified or end-modified linearized doggy bone DNA.

In a fifth aspect, the present invention is directed to an automated apparatus for RNA manufacturing, comprising an aforementioned bioreactor of the first aspect or a module of the forth aspect, wherein the apparatus further comprises at least one of a module for DNA synthesis and a module for RNA formulation.

In an embodiment, the module for DNA synthesis is configured to generate sufficient amount of DNA suitable for use in a bioreactor of aspect 1 or the module for transcribing DNA template into RNA of aspect 2. In a preferred embodiment, the module for DNA synthesis may comprise a thermocycler element for PCR-based DNA amplification and an element for purifying obtained PCR products. Suitably, said module for DNA synthesis may generate biotinylated DNA templates, preferably PCR-based biotinylated DNA templates.

In an embodiment, the module for RNA formulation is configured to generate lipid nanoparticle (LNP) encapsulated RNA. Accordingly, the module for RNA formulation comprises an LNP formulation module, wherein said LNP formulation module may comprise e.g. a pump element (e.g. a syringe pump), a tangential flow element, and a filtration element (e.g. comprising a sterile filter).

In an embodiment, the module for RNA formulation is configured to generate an RNA complexed with a polycationic peptide or protein (e.g. protamine or a polymeric carrier, e.g. a polyethylene glycol/peptide polymer e.g. according to WO2012/013326). Accordingly, the module for RNA formulation comprises at least one of a Protamine formulation/complexation and/or a module polyethylene glycol/peptide polymer formulation/complexation module. In that context, the module for RNA formulation may suitably use methods and means according to WO2016165825A1 and/or WO2018041921A1.

In an embodiment, the automated apparatus is arranged in a closed container and preferably in a single container, wherein the container comprises a unit for laminar airflow generation. Such configuration within a single container in particular helps to save space, in addition to equipment and personnel. Moreover, said automated apparatus may be configured to be portable, e.g. dimensioned in a way to allow transportation to regions of an outbreak of a pandemic.

In an embodiment, the automated apparatus further comprises at least one of a DNA immobilization module e.g. for immobilizing plasmid DNA, e.g. as described in PCT/EP2017/084264 or PCT/EP2018/086684, a DNA linearization module e.g. for linearization of plasmid DNA or doggy bone DNA, a RNA capping module e.g. for adding a cap0 or cap1 structure to in vitro transcribed RNA, a RNA polyadenylation module e.g. for adding a polyA tail to in vitro transcribed RNA, an RNA mixing module e.g. for mixing at least two different RNA species, an RNA spray drying module e.g. for generating spray-dried or freeze-spray dried RNA e.g. according to WO2016/184575 or WO2016184576, an RNA lyophilization module for generating lyophilized RNA e.g. according to WO2016/165831 or WO2011/069586, and/or a module for end-product storage.

In an embodiment, the automated apparatus further comprises at least one of an NGS (next generation sequencing) module e.g. for sequence analysis, a mass-spectrometry (MS) module, a quality control module (e.g. comprising an HPLC unit for analytical HPLC), a qPCR or ddPCR module, a capillary electrophoresis module, a media supply rack or a media supply module, a documentation module and/or a module for computer assisted control for all processing steps and interfaces for higher order controls and documentation systems.

In summary, devices and methods for the economical, controllable, reproducible, continuous (repeated batch), and GMP-compatible RNA production are presented. Described methods and means allow for repetitive use of DNA templates in several RNA (mass) production processes. The devices as described above therefore allow, for instance, for an accelerated production of RNA manufacturing. Further, an automated and, due to an appropriate size, portable RNA production apparatus as described above is advantageous in context of production of RNA therapeutics in a region of an outbreak of a pandemic.

It shall be understood that the bioreactor for RNA in vitro transcription, the method for RNA in vitro transcription, the use of a bioreactor according to the method, the module for transcribing DNA into RNA, and the automated apparatus for RNA manufacturing according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

The Figures shown in the following are merely illustrative and shall describe the present invention in a further way. These figures shall not be construed to limit the present invention thereto.

FIG. 7A-C show schematic views of a bioreactor according to another embodiment of the present invention.

FIG. 8A-C show schematic views of a bioreactor according to another embodiment of the present invention.

FIG. 9A-H show schematic views of a bioreactor according to another embodiment of the present invention.

DEFINITIONS

Figure 1:
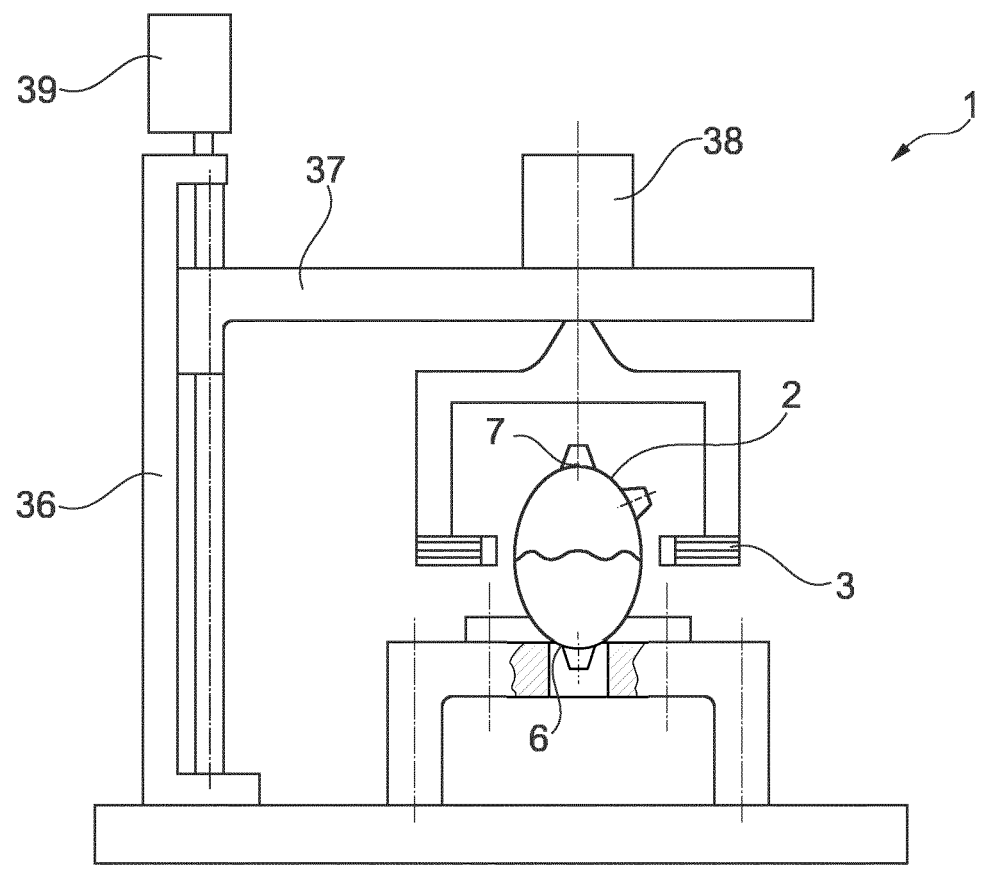
FIG. 1 shows a schematic view of a bioreactor according to an embodiment of the present invention.

For the sake of clarity and readability the following definitions are provided. Any technical feature mentioned for these definitions may be read on each and every embodiment of the invention. Additional definitions and explanations may be specifically provided in the context of these embodiments.

Doggybone, Doggy Bone DNA:

The term "Doggybone™" (dbDNA) as used herein denotes a minimal, closed-linear DNA vector enzymatically developed by Touchlight Genetics Ltd. The linear DNA is rapidly produced, plasmid-free and synthesized through an enzymatic process that yields a vector cassette containing only the encoded sequence of interest, promoter, e.g. poly A tail and telomeric ends.

Mixing:

In the context of the invention, "mixing" is typically a process that involves manipulation of a heterogeneous physical system with the intent to make it more homogeneous. Mixing is performed to allow mass transfer to occur between one or more streams, components or phases. Mixing is fundamentally the evolution in time of spatially dependent concentrations toward a more homogeneous state.

In the context of the present invention, a magnet unit is used, which allows in cooperation with magnetic particles and/or DNA magnetic particles for an improved mixing of components contained in the reaction vessel as defined herein, preferably without exerting any mechanical stress (such as shear stress) on said components. In particular, conventional mixing means that are known to induce mechanical stress on the components to be mixed are preferably avoided according to the present invention. For example, the mixing of fluids is preferably performed without shaking and/or agitating the reaction vessel. Instead, the magnet unit is configured to generate appropriate magnetic fields which lead to forces acting on magnetic particles and/or DNA magnetic particles, such that the latter particles start a movement within the reaction vessel, thereby leading to a mixing of the components contained in the reaction vessel.

The induced movement of the magnetic particles and or DNA magnetic particles may introduce turbulences in the components contained in the reaction vessel that are not caused by shaking or vibrating which allows for an improved mixing of the components in the reaction vessel to generate a homogeneous composition.

RNA In Vitro Transcription:

The term "RNA in vitro transcription" relates to a process wherein RNA is synthesized in a cell-free system. RNA may be obtained by DNA-dependent RNA in vitro transcription of an appropriate DNA template, which according to the present invention may be a linearized plasmid DNA template or a PCR-amplified DNA template. The promoter for controlling RNA in vitro transcription can be any promoter for any DNA-dependent RNA polymerase. Particular examples of DNA-dependent RNA polymerases are the T7, T3, SP6, or Syn5 RNA polymerases.

The DNA template (e.g., plasmid DNA, doggy bone DNA) may be linearized with a suitable restriction enzyme and immobilized on magnetic beads (e.g. as described in PCT/EP2017/084264 or PCT/EP2018/086684) before it is subjected to RNA in vitro transcription. Alternatively, the DNA template may be provided as PCR amplified DNA immobilized on magnetic particles (using biotinylated primers for PCR-based DNA template amplification and subsequent immobilization on streptavidin magnetic beads).

Reagents used in RNA in vitro transcription typically include: a DNA template (linearized DNA or linear PCR product) with a promoter sequence that has a high binding affinity for its respective RNA polymerase such as bacteriophage-encoded RNA polymerases (T7, T3, SP6, or Syn5); ribonucleotide triphosphates (NTPs) for the four bases (adenine, cytosine, guanine and uracil); optionally, a cap analogue (e.g. m7G(5')ppp(5')G(m7G) or a cap analogue derivable from the structure disclosed in claim 1-5 of WO2017/053297 or any cap structures derivable from the structure defined in claim 1 or claim 21 of WO2018075827); optionally, further modified nucleotides as defined herein; a DNA-dependent RNA polymerase capable of binding to the promoter sequence within the DNA template (e.g. T7, T3, SP6, or Syn5 RNA polymerase); optionally, a ribonuclease (RNase) inhibitor to inactivate any potentially contaminating RNase; optionally, a pyrophosphatase to degrade pyrophosphate (inhibitor of RNA synthesis); MgCl2, which supplies Mg2+ ions as a co-factor for the polymerase; a buffer (TRIS or HEPES) to maintain a suitable pH value, which can also contain antioxidants (e.g. DTT), and/or polyamines such as spermidine at optimal concentrations, e.g. a buffer system comprising Citrate and/or betaine as disclosed in WO2017/109161.

The nucleotide mixture used in RNA in vitro transcription may additionally contain modified nucleotides as defined herein. In that context, preferred modified nucleotides comprise pseudouridine (ψ), N1-methylpseudouridine (m1ψ), 5-methylcytosine, and 5-methoxyuridine. The nucleotide mixture (i.e. the fraction of each nucleotide in the mixture) used for RNA in vitro transcription reactions may be optimized for the given RNA sequence, preferably as described in WO2015188933.

RNA In Vitro Transcription Master Mix, IVT Master Mix:

An RNA in vitro transcription (IVT) master mix may comprise the components necessary for performing an RNA in vitro transcription reaction as defined above. Accordingly, an IVT master mix may comprise at least one of the components selected from a nucleotide mixture, a cap analogue, a DNA-dependent RNA polymerase, an RNAse inhibitor, a pyrophosphatase, MgCl2, a buffer, an antioxidant, betaine, Citrate.

Semi-Permeable Filter:

A filter, which allows certain particles to pass through the pores of the filter material when the particles are smaller than the pore size, thereby preventing transmission of particles larger than the filter material pore size.

If hereinafter a group is defined to comprise at least a certain number of embodiments, this is also meant to encompass a group which preferably consists of these embodiments only.

As used in the specification and the claims, the singular forms of "a" and "an" also include the corresponding plurals unless the context clearly dictates otherwise.

It needs to be understood that the term "comprising" is not limiting. For the purposes of the present invention, the term "consisting of" is considered to be a preferred embodiment of the term "comprising of".

DETAILED DESCRIPTION OF THE FINDINGS UNDERLYING THE PRESENT INVENTION

The invention relates to a bioreactor for RNA in vitro transcription configured to be operable in an automated manner under GMP-compliant conditions. A schematic drawing of a bioreactor for RNA in vitro transcription according to an embodiment of the invention is provided i.a. in FIGS. 1 and 7.

The bioreactor 1 comprises a reaction vessel 2 for holding magnetic particles, DNA templates, a DNA immobilisation buffer, DNA magnetic particles and an IVT master mix. The inner surface 21 of the reaction vessel 2 has an egg-shape inner geometry. Alternatively, the inner surface 21 of the reaction vessel 2 according to the present invention may be ellipsoidal or oval. In any case, it is preferred that the inner surface 21 of the reaction vessel 2 has a shape without edges. This may be particularly important for the mixing properties of the bioreactor 1. Moreover, said ellipsoid, oval or egg shape, in particular the absence of edges, is advantageous for cleanability (important for GMP compatibility) and reduces the risk of formation of unwanted precipitations in the bioreactor. Moreover, the egg shape has the advantage over e.g. flat round shape that the fluids (e.g. the RNA product) may easily flow off the bioreactor 1 via a medium port 6 into a medium pipe 66 (see also FIG. 11).

Further, the above described inner geometries help to prevent sticking and drying out of e.g. proteinaceus residues at the inner surfaces, as generally a shape without edges, and more particularly an ellipsoidal, oval or egg shape supports a good drain off of fluids. In addition, the ellipsoidal, oval or egg shape has the advantage over e.g. a "cone shape" that the risk is minimized that DNA magnetic particles assemble at the bottom of the reactor which may reduce the yield of the RNA in vitro transcription (e.g. those DNA templates would not be accessible for RNA polymerases) or clog the medium port 6. To further prevent clogging of the medium port 6 liquid may be flushed in regular intervals through the medium port 6 into the bioreactor 1 during transcription reaction. Those flushes may additionally improve the mixing properties of the biochemical reaction in the bioreactor (e.g. IVT reaction, DNA immobilization reaction).

The bioreactor 1 is configured to allow repetitive RNA in vitro transcription reactions on DNA templates that are immobilized on free-floating magnetic particles ("DNA magnetic particles"). For example, DNA templates may be provided as PCR amplified DNA that is immobilized on magnetic beads (using biotinylated primers for PCR-based DNA template amplification and subsequent immobilization on streptavidin magnetic beads) or linearized plasmid DNA that is immobilized on magnetic beads (e.g. as described in PCT/EP2017/084264 or PCT/EP2018/086684).

The bioreactor 1 further comprises a magnet unit 3 positioned at the reaction vessel 2. The magnet unit 3 enables contactless mixing of the reaction containing magnetic particles or DNA magnetic particles, implying that no mixing means have to be implemented in the mixing process, which is an advantageous feature in the context of sufficient cleanability of the bioreactor 1 e.g. in pharmaceutical production of RNA. Moreover, mixing of the RNA in vitro reaction may be performed without rotation/shaking of the bioreactor 1. This is particularly advantageous as rotation or shaking would be strongly impaired due to different inlet and outlet ports that have to be mounted on the bioreactor 1.

Further, the magnet unit 3 may be used for capturing DNA magnetic particles before starting another cycle of RNA in vitro transcription thereby allowing repeated batch RNA in vitro transcription (IVT) on the same DNA template which dramatically reduces overall RNA production costs. Further, the magnet unit 3 may be used for removing DNA magnetic particles for final cleaning or sanitizing of the bioreactor 1. Accordingly, DNA may be removed without the need of enzymatic DNAse treatment which (i) reduces costs as no such enzyme is needed, (ii) reduces the risk of contaminating the final RNA product with a further component (that is DNAse), and (iii) reduces the risk of contaminating the final RNA product with DNA fragments or partially digested DNA fragments.

In FIG. 1, the magnet unit 3 is formed in a ring shape (see also FIG. 4) and receives the reaction vessel 2 in a centre 33 of the magnet unit 3 such that the magnet unit 3 may rotate around the reaction vessel 2. The magnet unit 3 is attached to a spindle axis 36 via an arm 37, wherein the spindle axis 36 may move the magnet unit 3 in a vertical direction. By vertically moving the magnet unit 3, a magnet field can be generated along a longitudinal direction of the reaction vessel 2. Accordingly, a homogeneous mixing of components in the reaction vessel 2 may be realised by inducing the magnetic particles both in a radial direction and in a longitudinal direction. A rotation driving means 38 for the magnet unit 3 is arranged on the arm 37 directly above the reaction vessel 2 and a driving means 39 to operate the spindle axis 36 is arranged directly at the spindle axis 36.

Figure 2:
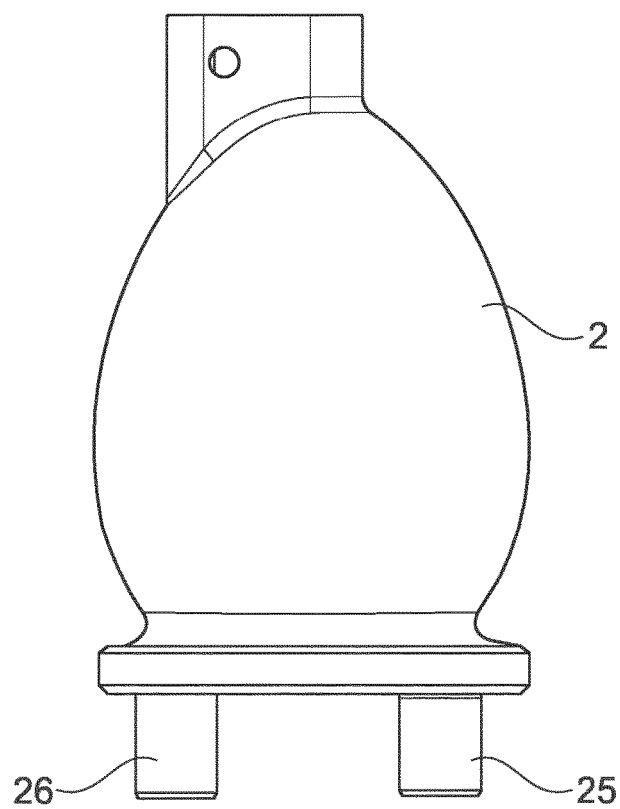
FIG. 2 shows a schematic view of a reaction vessel according to an embodiment of the present invention.
Figure 3A:
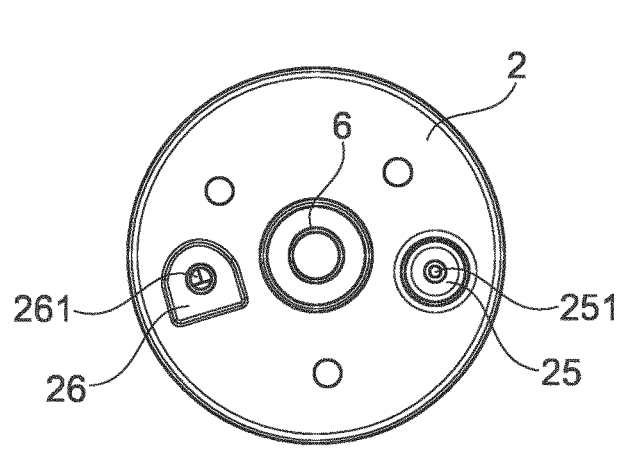
FIGS. 3A, B show schematic views of a reaction vessel according to an embodiment of the present invention.
Figure 3B:
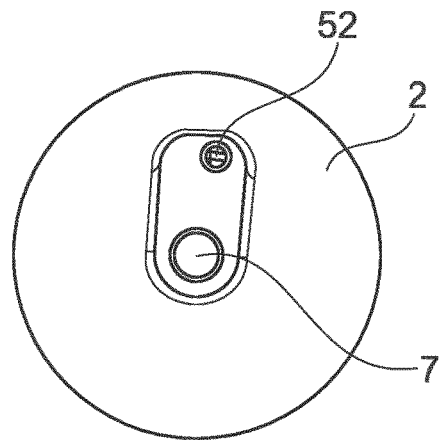

FIG. 2 shows the reaction vessel 2 in a perspective view, FIG. 3A shows a bottom view of the reaction vessel 2 and FIG. 3B shows a top view of the reaction vessel 2. The reaction vessel 2 may be made of a material such as titan, which is chemically resistant, resistant to extreme temperatures, extreme pH values, mechanical forces and/or corrosion.

In all embodiments of the bioreactor 1 according to the present invention, the inner surface 21 of the reaction vessel 2 has a shape without edges, preferably an ellipsoid, oval or egg shape. It is further preferred that the inner surface 21 of the reaction vessel 2 is polished with a value Ra<=0.8. A suitable way to obtain such Ra values is known to the skilled in the art. For instance, the inner surface 21 may be mechanically polished, electro polished, or chemically polished or the like.

Figure 11:
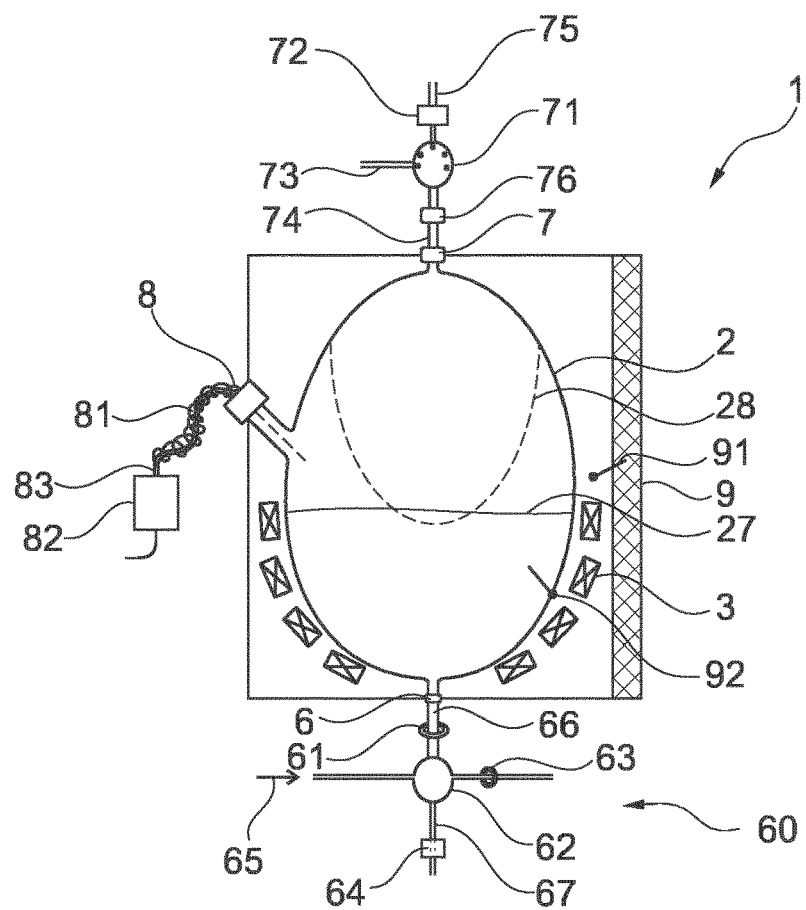
FIG. 11 shows a schematic partial section view of a bioreactor according to another embodiment of the present invention.

As shown in FIG. 3B, the reaction vessel 2 comprises an exit port 7 for exhaust gas or waste fluids. The exit port 7 may e.g. be used for venting of the reaction vessel 2 during filling of the vessel. To this end, the exit port 7 is arranged at the uppermost point of the reaction vessel 2. At a top portion of the reaction vessel 2, a first end 52 of a heat exchange channel 51 of a temperature element 5 is arranged. As shown in FIG. 11, the exit port 7 may be connected to at least one of an exhaust duct 73 and a waste channel 74. For instance, the exit port 7 may be connected to at least both, the exhaust duct 73 and the waste channel 74, by a multi position valve. The exit port 7 may allow for receiving and venting exhaust gas or exhaust gases emerging within the reaction vessel 2. In case of a waste fluid or a cleaning fluid, the exit port 7 may serve for draining the fluid out of the reaction vessel 2. The exit port, the exhaust duct and/or the waste channel may hold at least one means for measuring and/or adjusting pressure.

Further, a medium port 6 is arranged at a lowermost point of the reaction vessel 2 and may be further connected to a valve means 60 guiding a supplying or draining of components (in FIG. 3A). The reaction vessel 2 comprises two legs 25, 26, which may support the reaction vessel 2 vertically. Further, each leg 25, 26 comprises a conduit 251, 261 extending through the legs 25, 26. Accordingly, the first leg 25 comprises a first conduit 251 configured to be in a fluid communication with the valve means 60 and the second leg 26 comprises a second conduit 261 configured to be in a fluid communication with a second end 53 of a heat exchange channel 51 of a temperature element 5 (see FIGS. 7B and 7C).

Figure 4:
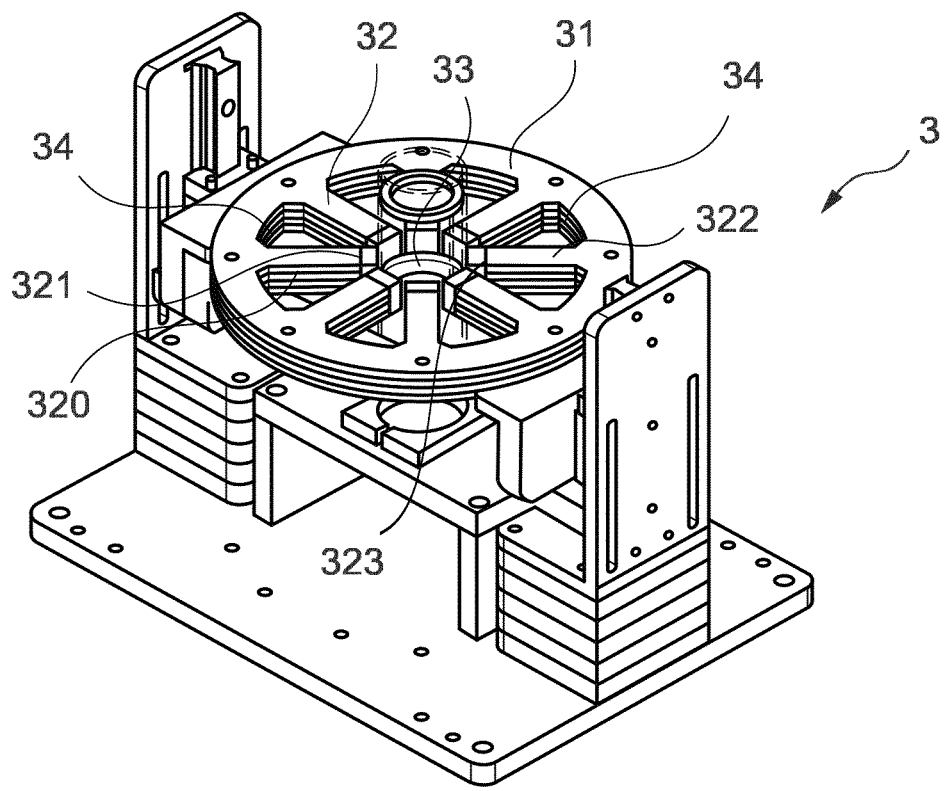
FIG. 4 shows a schematic view of a magnet unit according to an embodiment of the present invention.

FIG. 4 shows a preferred embodiment of the magnet unit 3. The magnet unit 3 is formed in a star-shape comprising a magnetic ring 31 and a plurality of rods 32. The magnetic ring 31 and the rods 32 may be made of a plurality of magnetisable laminated electrical sheets, thus form a laminated stack for shielding periphery components from the magnet field. The magnet ring 31 is designed to surround the reaction vessel 2. In other words, the reaction vessel 2 can be positioned in the centre 33 of the magnetic ring 31.

Figure 5:
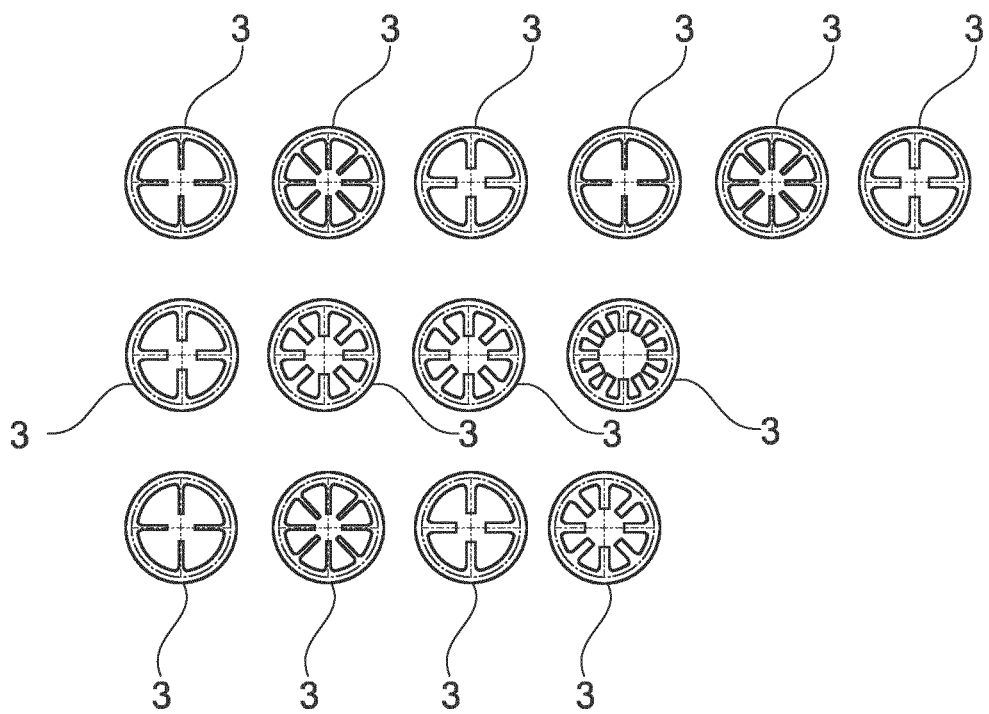
FIG. 5 shows a schematic view of magnet rings according to another embodiment of the present invention.

The magnetic ring 31 comprises a first rod 320 and a second rod 322 extending from an inner circumference 34 of the magnetic ring 31 to a centre 33 of the magnetic ring 31, so that free ends 321, 323 of the first and second rod 320, 322 face each other. The free end 321 of the first rod 320 comprises a magnet with an N pole and the free end 323 the second rod 322 comprises a magnet with an S pole. As shown in FIG. 5, however, the number and length of rods 32 can vary. The rods 32 are arranged at the inner circumference 34 of the magnetic ring 31 and extend in a direction to the centre 33 of the magnetic ring 31. The plurality of the rods 32 are arranged in a star shape and evenly spaced apart from each other, such that the magnetic ring 31 is formed symmetrically. At each free end of the rods 32, a magnet with an N pole and a magnet with an S pole is alternately arranged.

Figure 6:
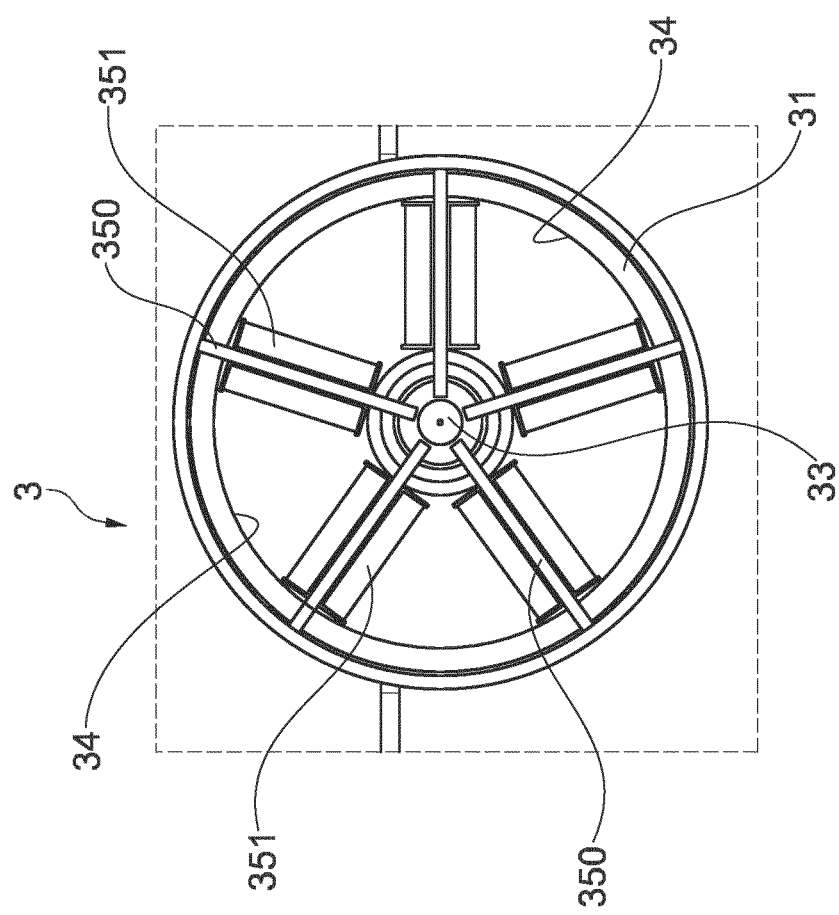
FIG. 6 shows a schematic view of a magnet unit according to another embodiment of the present invention.

Alternatively, as shown in FIG. 6, the magnet unit 3 comprises a magnet ring 31 including a plurality of guide plates 350 and electric coils 351. The star-shaped guide plates 350 extend from the inner circumference 34 of the magnetic ring 31 to the centre 33 of the magnetic ring 31. Each guide plate 350 comprises an electric coil 351 for generating a magnetic field. The magnet ring 31 is surrounded by a housing having cooling means 352. The cooling means 352 are integrated in the housing of the magnetic ring along the circumference of the magnetic ring 31 to carry away heat generated by the high current passing through the electromagnetic coils. The cooling means 352 may be a cooling channel in which a cooling medium such as water is provided.

Figure 7A:
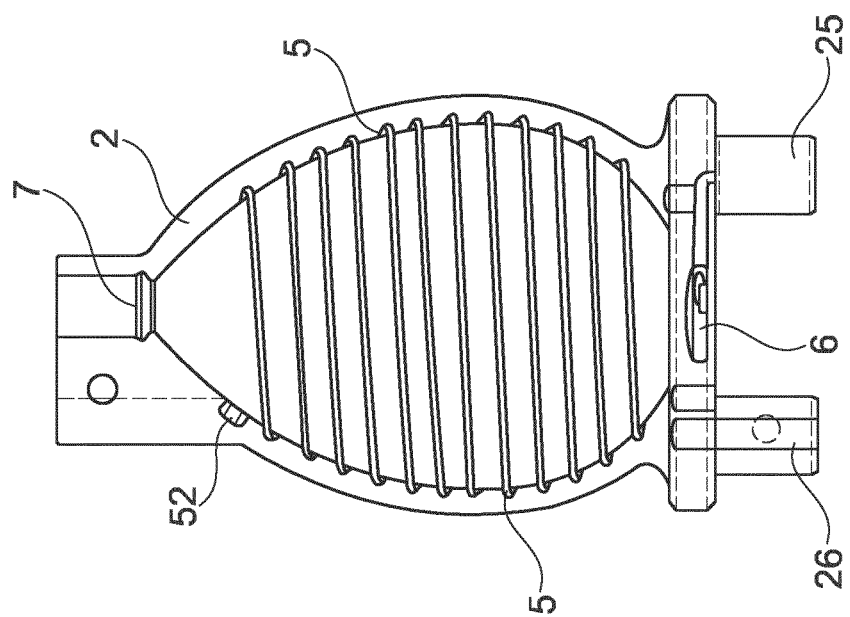

FIGS. 7A to 7C show another preferred embodiment of a bioreactor 1. The reaction vessel 2 may be made of a solid material and comprises an inner surface 21 and an outer surface 23. Between the inner surface 21 and the outer surface 23 a temperature element 5 is integrated for adjusting a temperature of the reaction vessel 2. The temperature element 5 comprises a heat exchange channel 51 helically surrounding the reaction vessel 2 in the radial direction relative to a longitudinal axis of the reaction vessel 2. To facilitate manufacturing of such reaction vessel 2 with a complex geometry, the reaction vessel 2 may be manufactured by means of additive manufacturing.

The heat exchange channel 51 comprises a first end 52 and a second end 53 fluidly connected to the second conduit 261 in the second leg 26. The first end 52 is arranged at the top portion of the reaction vessel 2, however, positioned offset from the uppermost top or the exit port 7 to secure a reliable accessibility of the exit port 7. The second end 53 of the heat exchange channel is arranged at the bottom portion of the reaction vessel 2, however, positioned offset from the lowermost bottom or the medium port 6 to secure a reliable accessibility of the medium port 6. Through the first end 52 or second end 53 a heat exchange medium such as water can be supplied into the heat exchange channel 51 for heating or cooling the components inside the reaction vessel 2.

FIGS. 8A and 8B show an alternative embodiment of the temperature element 5. The temperature element 5 comprises a heating wire 54 at least partially, preferably completely, helically surrounding the reaction vessel 2 in a radial direction relative to the longitudinal axis of the reaction vessel 2. The heating wire 54 is at least partially integrated in an outer surface 23 of the reaction vessel 2 (in FIG. 8A). Additionally or alternatively, the outer surface 23 of the reaction vessel 2 may be coated with a heat isolation material 55 and the heating wire 54 is at least partially retracted in the heat isolation material 55 (in FIG. 8B).

Referring to FIGS. 7B and 7C, the reaction vessel 2 comprises at least one, preferably two flow breakers 24 arranged at least partially along the inner surface 21 of the reaction vessel 2 in a longitudinal direction of the reaction vessel 2. The flow breaker 24 may disturb a uniform flow of the components in the reaction vessel 2 and can thereby improve mixing. Moreover, the flow breaker 24 may prevent sedimentation of the magnet particles when the magnet unit 3 stops rotating and/or changes rotation direction. Two flow breakers 24 are spaced apart from each other in a radial direction relative to the longitudinal axis of the reaction vessel 2.

As shown in FIGS. 9A to 9H, the flow breaker 24 may be rib-shaped and protrude from the inner surface 21 of the reaction vessel 2 along the longitudinal direction of the reaction vessel 2. In another embodiment, the flow breaker 24 is arc-shaped and comprises a T-shaped cross section (in FIGS. 9A and 9B) or a L-shaped cross section (in FIGS. 9E and 9F). In yet another embodiment, the flow breaker 24 is corrugated or wave-shaped (in FIGS. 9C and 9D). Alternatively, the flow breaker 24 comprises a plurality of protrusions in a semi-circle shape spaced apart from each other at the inner surface 21 of the reaction vessel 2 along the longitudinal direction (in FIGS. 9G and 9H).

Figure 10:
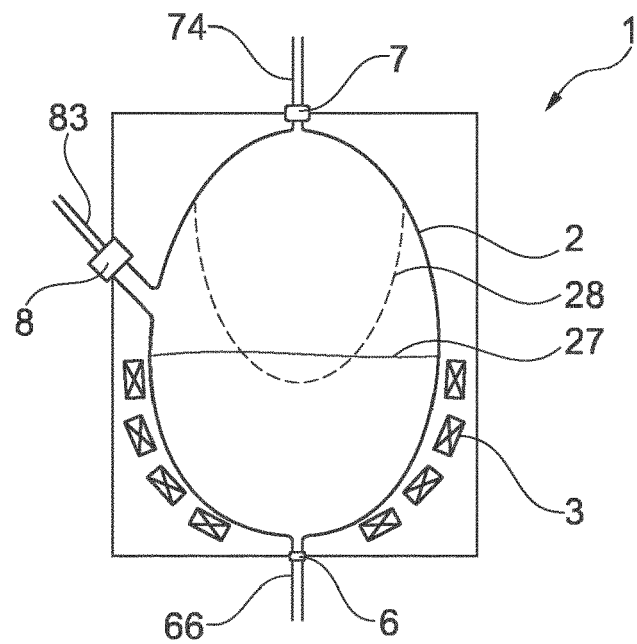
FIG. 10 shows a schematic partial section view of a bioreactor according to another embodiment of the present invention.

Notably, elements and features of the bioreactor 1 of the invention mentioned in the context of FIGS. 10 to 12 may likewise be part of the reactor shown in FIGS. 1 to 9 even if not explicitly mentioned herein. Accordingly, the bioreactor 1 as illustrated in FIGS. 1 to 9 may also comprise at least one selected from magnetic trap 61, Hall sensor 63, flow cell 64, temperature sensor 91, additional sensor 92, or a specific filling level 27 or a maximal fluid amplitude 28.

FIG. 10 shows another embodiment of the bioreactor 1. The bioreactor 1 in FIG. 10 comprises an array of electromagnets 3 positioned on the outer surface of the reaction vessel. The array of electromagnets 3 allows for mixing of the reaction (by circulation of magnetic particles or DNA magnetic particles in the reaction) which is caused by periodic activation of said array of electromagnets 3. This enables contactless mixing of the reaction containing magnetic particles or DNA magnetic particles, implying that no mixing means have to be implemented in the mixing process, which is an advantageous feature in the context of sufficient cleanability of the bioreactor 1 e.g. in pharmaceutical production of RNA. Moreover, mixing of the RNA in vitro reaction may be performed without rotation/shaking of the bioreactor 1. This is particularly advantageous as rotation or shaking would be strongly impaired due to different inlet and outlet ports that have to be mounted on the bioreactor 1. Further, said array of electromagnets 3 may be used for capturing DNA magnetic particles before starting another cycle of RNA in vitro transcription thereby allowing repeated batch RNA in vitro transcription (IVT) on the same DNA template which dramatically reduces overall RNA production costs. Further, said array of electromagnets 3 may be used for removing DNA magnetic particles for final cleaning or sanitizing of the bioreactor 1. Accordingly, DNA may be removed without the need of enzymatic DNAse treatment which (i) reduces costs as no such enzyme is needed, (ii) reduces the risk of contaminating the final RNA product with a further component (that is DNAse), and (iii) reduces the risk of contaminating the final RNA product with DNA fragments or partially digested DNA fragments.

Further shown in FIG. 10 is a filling level 27 of a fluid hold in the reaction vessel 2. Additionally, the dashed line shows a maximal fluid amplitude 28. Thereby, the maximal fluid amplitude 28 is understood to be the amplitude a fluid contained in the reaction vessel 2 and brought into a shaking or rotational movement maximally reaches on the inner surface 21 of the reaction vessel 2. The bioreactor 1 further comprises an inlet port 8 arranged at the reaction vessel which allows for filling media into the reaction vessel 2. As can be seen in FIG. 11, the inlet port 8 is arranged laterally on the reaction vessel 2 and below the level of a maximal fluid amplitude 28 on the inner surface 21 of the reaction vessel 2. This configuration may help to prevent that e.g. protein residues deposit and harden on the inner surface 21 of the reaction vessel 2, which might be the case of the inlet port is arranged above a maximal fluid amplitude. In the latter case, residues from a filling of the reaction vessel 2 might deposit e.g. at and/or around the inlet port. Moreover, the lateral position of the inlet port 8 close to the filling level 27 allows a filling media into the reaction vessel without unwanted formation of splashes that may form residues deposit and harden on the inner surface 21 of the reaction vessel. Upstream the inlet port 8, an inlet pipe 83 for guiding filling media towards the inlet port 8 and into the reaction vessel 2 is arranged. The bioreactor 1 further comprises a waste port 7 for exhaust gas or waste fluids. The waste port 7 may e.g. used for venting of the reaction vessel 2 during filling of the vessel. To this end, the waste port 7 is arranged at the uppermost point of the reaction vessel 2. Downstream the waste port 7, a waste channel 74 is arranged which allows to uptake exhaust gas or waste fluids which leave the vessel 2 through the waste port 7. Further, an outlet port 6 is arranged at the lowermost point of the reaction vessel 2, thereby allowing a convenient duct or drain of fluids through the outlet port 6 in order to further guide these fluids through an outlet pipe 66.

FIG. 11 shows another preferred embodiment of a bioreactor 1 according to the present invention. Apart from the components already shown in FIG. 1-10—namely e.g. a reaction vessel 2 and a magnet unit 3, a waste port 7, a waste channel 74, an outlet port 6, an outlet pipe 66 an inlet port 8, an inlet pipe 83 as well as a filling level 27 referring to a contact line of a fluid surface at the inner surface of the reaction vessel 2 and a maximal fluid amplitude 28—the embodiment in FIG. 11 additionally comprises a magnetic trap 61 positioned at the outlet port 6 to minimize the risk of contaminating the RNA product with DNA magnetic particles and/or DNA magnetic particles. This implies that the magnetic trap 61 helps to retain the magnetic particles and/or the DNA magnetic particles within the reaction vessel 2 when draining a produced RNA out of the reaction vessel 2 through the outlet port 6. The magnetic trap 61 may, for instance, at least partially surround the outlet port 6 or the outlet pipe 66 downstream abutting the outlet port 6. Preferably, the magnetic trap 61 may be a ring magnet, e.g. an electromagnet in form of a ring. Downstream the outlet port 6 and the magnetic trap 61, a multi position valve 62 is arranged. The multi position valve 62 connects the outlet port 6, or the outlet pipe 66 downstream connected to the outlet port 6, with three further lines. The first out of the three lines serves for ducting the RNA containing fluid component after the RNA in vitro transcription reaction successfully has taken place. In order to monitor that no magnetic particles and/or DNA magnetic particles are contained in this component, a Hall sensor 63 is arranged downstream the multi position valve 62 at the first line. Accordingly, the Hall sensor 63 is configured for detecting unwanted magnetic fields in the RNA product. A second line connected to the outlet port 6 serves as a waste channel 67 for e.g. cleaning fluids. For monitoring purposes, a flow cell 64 is arranged at this second line. The third line connected to the multi position valve 62 may duct a process gas or a cleaning gas, e.g. N2 or a synthetic solution, in the direction indicated with arrow 65. The process gas or cleaning gas may be cyclically directed by the multi position valve 62 in direction of the outlet port 6. Thereby, a sedimentation of magnetic particles and/or DNA magnetic particles at the outlet port, leading to a clogging of the port, may be prevented.

Further, the bioreactor 1 comprises temperature elements, e.g. Peltier elements 9 to allow heating or cooling of the bioreactor 1° C. at 37° C., which is an optimal temperature for RNA in vitro transcription, and heating of the bioreactor 1° C. at 80° C., which is an optimal temperature for cleaning/sanitizing of the bioreactor 1. A temperature sensor 91 is further arranged at the reaction vessel 2 for monitoring the temperature in the reaction vessel 2. Further temperature sensors may be positioned at the inner surface 21 of the reaction vessel and/or in proximity to the reaction vessel (e.g., at the inlet port or outlet port). For instance, an additional sensor 92 may be positioned inside the reaction vessel 2 for measuring, for example, the temperature, the pH value or the salt concentration.

Still referring to FIG. 11, the bioreactor 1 further comprises a multi position valve 71 arranged downstream the waste port 7 and the waste channel 74 abutting the waste port 7. Via the multi position valve 71, the waste port 7 and waste channel 74 are connected to a line for waste fluid with a waste flow cell 72 arranged at this line for monitoring the flow of waste fluids. Further, the multi position valve 71 connects the waste port 7 and waste channel 74 to an exhaust duct 73 for exhaust gases, which may, e.g. emerge during filling or cleaning of the reaction vessel 2. Optionally, there may be a pressure sensor 76 arranged at the waste port or the waste channel 74 for measuring the pressure at the waste port 7 and/or in the waste channel 74. At the inlet pipe 83 upstream the inlet port 8, a heating 81, exemplarily shown as a heating coil, is arranged around the inlet pipe. Upstream the pipe section with the heating 81, a heating flow cell is arranged for monitoring the feed of the components into the reaction vessel 2. Said heating 81 may be used for adjusting the media filled into the reactor to the desired optimal temperature (e.g., 37° C. for RNA in vitro transcription).

Figures 12A, 12B:
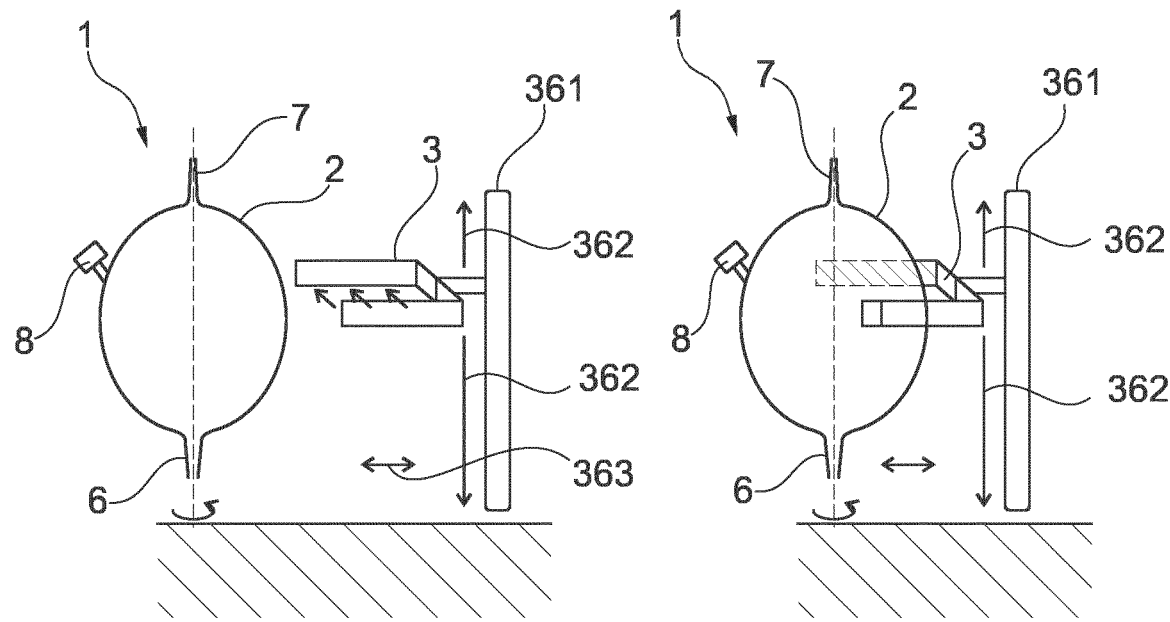
FIGS. 12A, B show schematic views of a bioreactor with a movable magnet unit according to an embodiment of the invention.
Figure 13:
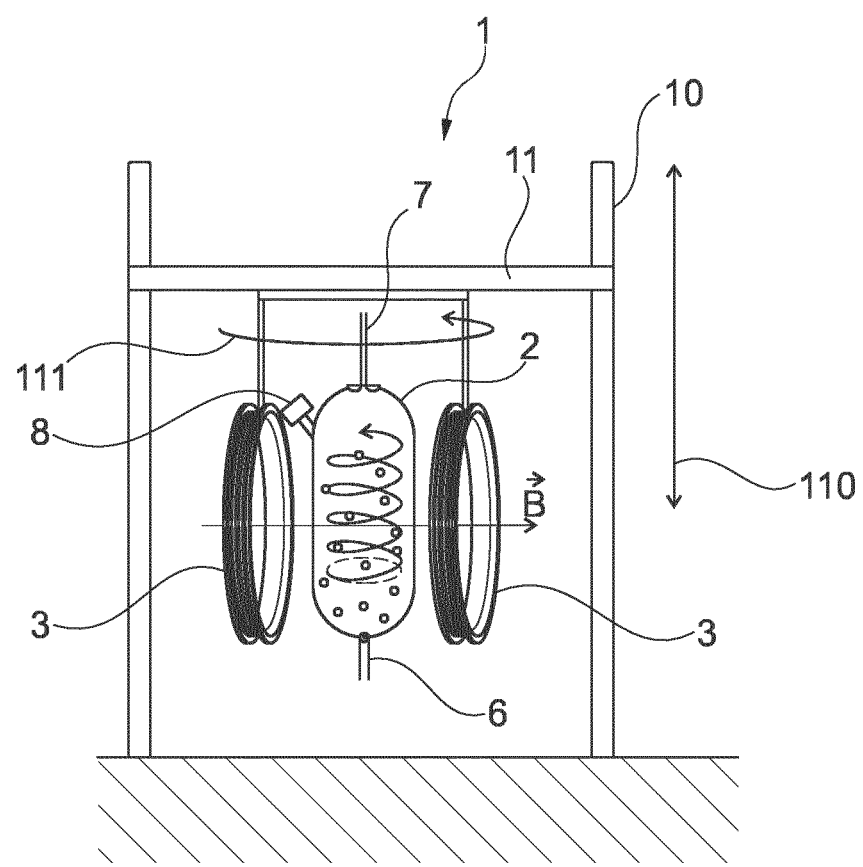
FIG. 13 shows a schematic view of a bioreactor with a rotatable magnet unit according to an embodiment of the invention.

FIGS. 12A and 12B as well as FIG. 13 shows the alternative designs of the magnet unit of a bioreactor 1 according to the present invention. Referring to FIGS. 12A and 12B, an embodiment of a bioreactor 1 is shown, comprising a reaction vessel 2 with outlet port 6, waste port 7, and inlet port 8 as well as a magnet unit 3. Notably, elements mentioned in the context of the bioreactor as specified in FIG. 11 may likewise be part of the reactor shown in FIGS. 12A, 12B (e.g., temperature sensor 91, hall sensor 63, flow cells 64, egg shape, etc.) even if not explicitly mentioned herein. The magnet unit 3 is realised in form of a magnet, preferably an electromagnet, or a permanent magnet, which can be moved towards and apart the reaction vessel 2 along a transversal axis of the reaction vessel 2, as indicated by the arrows 363 or controllable Helmholtz Coils. Further, the magnet unit 3 can be moved upwardly and downwardly along a longitudinal axis of the reaction vessel 2, as indicated by the arrows 362. To this end, the magnet unit 3 is mounted on a movable support 361, which allows the above described movement of the magnet unit 3. Additionally, as further indicated in FIGS. 12A and 12B, the reaction vessel 2 may be, in this embodiment, be rotatable around its vertical axis. Alternatively, the reaction vessel 2 may be mounted on a movable support (not shown), which allows the above described movement of the reaction vessel 2 relative to the magnet unit 3 (which may not be mounted on a movable support 361). Additionally, as further indicated in FIGS. 12A and 12B, the reaction vessel 2 may, in this embodiment, be rotatable around its vertical axis.

FIG. 12A shows the bioreactor 1 in a state where the magnet unit 3 is laterally removed from the reaction vessel 2, whereas in FIG. 12B a configuration is shown, where the magnet unit 3 is laterally in the closest position to the reaction vessel 2.

FIG. 13 shows an embodiment of the bioreactor 1 with a magnet unit 3 realized by at least two magnetic coils, which are rotatable around the reaction vessel as indicated by arrows 111 and rotatable arranged at horizontal bar 11 of a support 10. The horizontal bar 11 can be moved upwardly and downwardly, indicated by arrows 110, such that the position of the magnetic fields of the magnetic coils 3 at the reaction vessel 2 can be additionally varied. Notably, elements mentioned in the context of the bioreactor as specified in FIG. 1-11 may likewise be part of the reactor shown in FIG. 13 (e.g., temperature sensor 91, hall sensor 63, flow cells 64, egg shape, etc.) even if not explicitly mentioned herein.

Figure 14A:
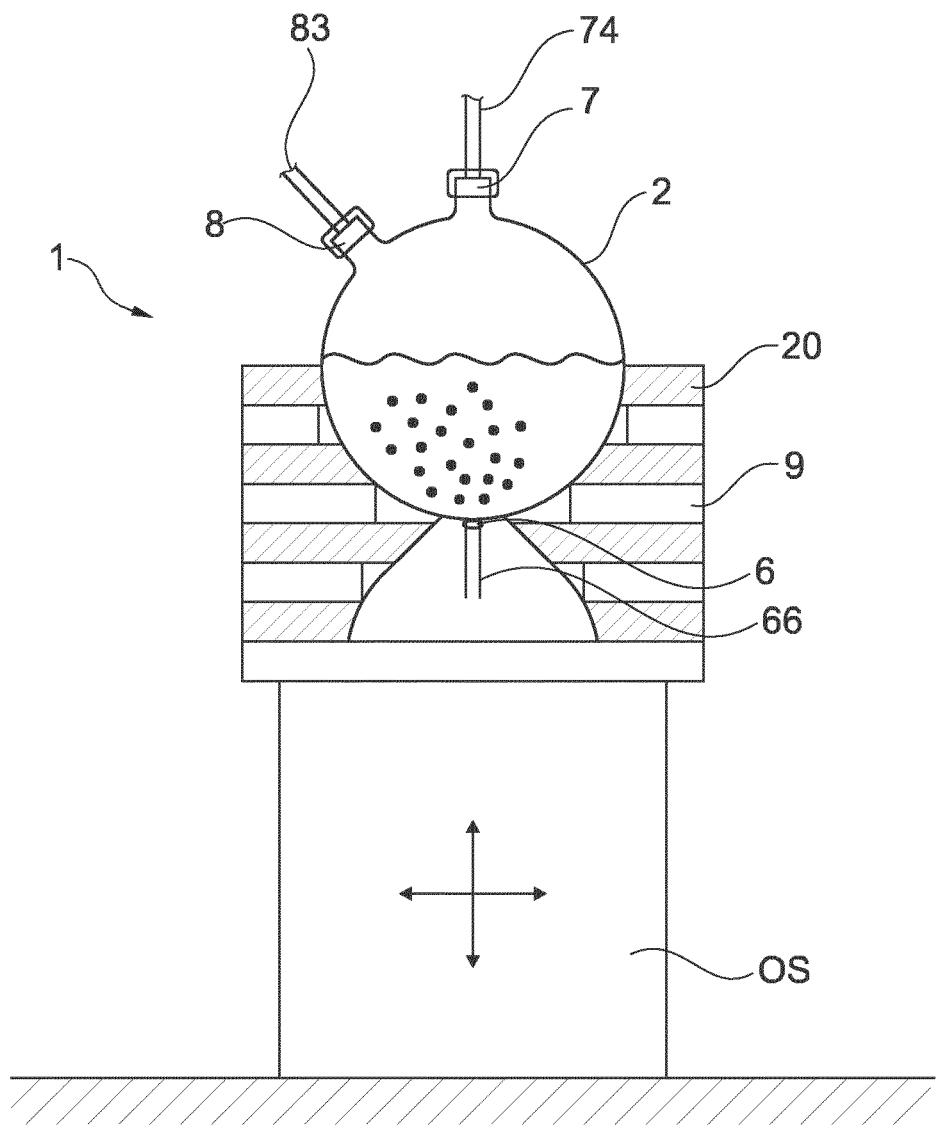
FIGS. 14A, B show schematic views of a bioreactor with an orbital shaker
Figure 14B:
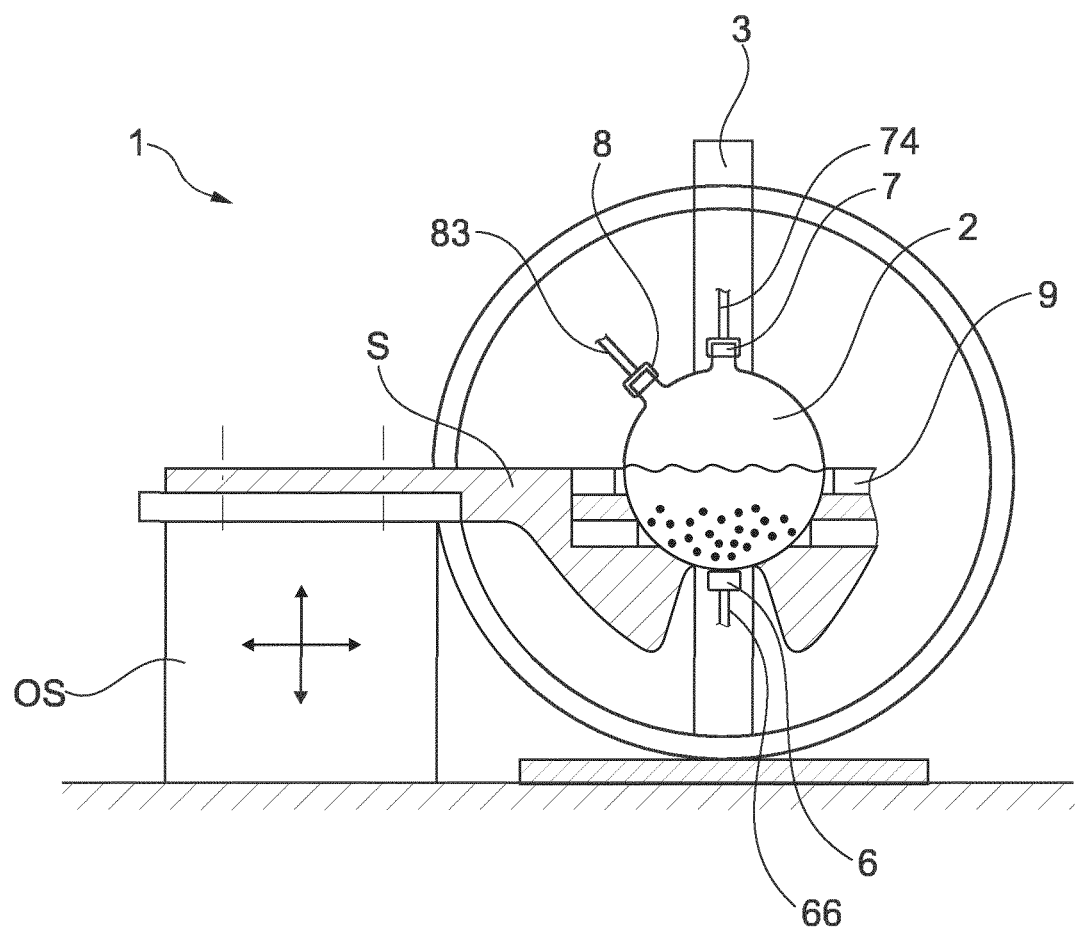

In FIGS. 14A and 14B embodiments of the bioreactor 1 are shown, which allow for a mixing or stirring of the components hold in the reaction vessel by mechanical motion introducing means as well as by either additionally directing a process gas or a process fluid into the reaction vessel or by a cooperation of the magnetic particles and a magnet unit.

Apart from the components already described in context of FIG. 11, FIG. 14A shows a bioreactor 1 with reaction vessel 2 positioned on an orbital shaker OS. Orbital shaker OS allows for a 3 dimensional movement of the reaction vessel, preferably with small amplitudes due to the connections for fluids, gas and sensors of the bioreactor, which shall not be damaged by a movement of the reaction vessel 2. For inducing a movement of the reaction vessel 2 by means of the orbital shaker OS, the former is placed on top of the orbital shaker OS. The reaction vessel 2 is laterally at least partially surrounded and may thereby be hold by a support 20. The support 20 contains Peltier elements 9 for heating and/or cooling the reaction vessel. Through the outlet port 6 and outlet pipe 66 in FIG. 14A, a process gas, preferably $N_2$, or alternatively a process fluid, may be guided into the reaction vessel 2, in order to introduce an additional movement for mixing/stirring the components hold in the reaction vessel 2. Outlet port 6 and outlet pipe 66 also serve to outlet media, e.g. the produced RNA, out of the reaction vessel. Through inlet pipe 83 and inlet port 8, media can be filled into the reaction vessel. Further, FIG. 14A shows a waste port 7 and waste channel arranged at the uppermost point of the reaction vessel.

In FIG. 14B, an embodiment of a bioreactor 1 is shown, which allows for mixing or stirring of the components hold in the vessel 2 by a cooperation of a Helmholtz coil and the magnetic particles, an orbital shaker OS and a direction of process gas or process fluid into the reaction vessel. To this end, an orbital shaker OS is connected via a horizontal support S with the reaction vessel 2, which is hold by the support S and which is positioned in the middle of a magnet unit 3. The magnet unit is here realized in form of a Helmholtz coil. Part of the support which holds the reaction vessel 2 contains recesses in which Peltier elements 9 are positioned. The Peltier elements are positioned close to or even touch the reaction vessel for efficient heating and/or cooling of the vessel. In addition to the aforementioned components, FIG. 14B shows an inlet port 8 and an inlet pipe 83, a waste port 7 and a waste channel 74, as well as an outlet port 6 and an outlet pipe 66, which latter elements are similar to those described in context of FIG. 11 and FIG. 14A.

Figure 15:
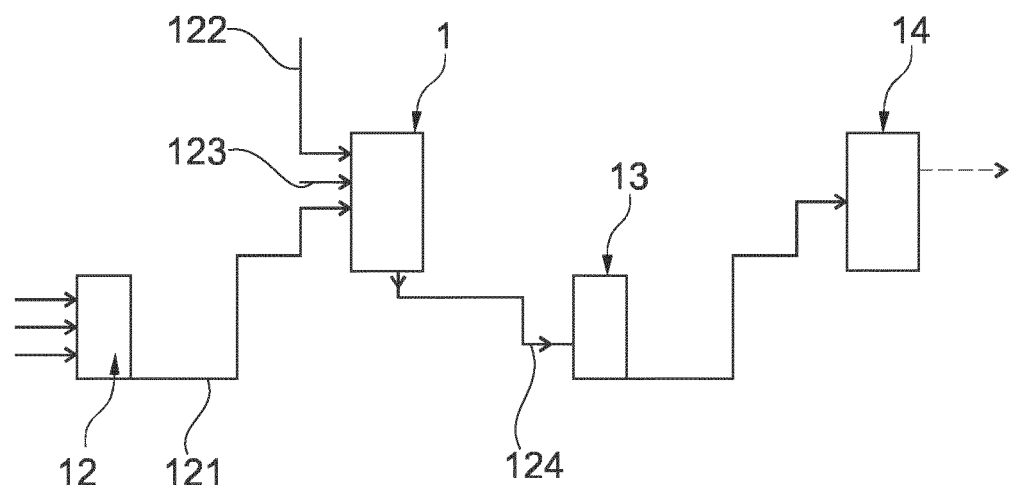
FIG. 15 shows exemplary components of a module for transcribing DNA into RNA.

In FIG. 15, an embodiment of the module for transcribing DNA into RNA is shown. It comprises a unit for preparing an IVT master mix 12, also referred to as pre-mixer. As indicated by the arrows incoming at the unit for preparing an IVT master mix 12, this unit 12 may be filled with an IVT buffer (HEPES, Tris), a nucleotide mixture (comprising nucleotides and, optionally, modified nucleotides), a DNA-dependent RNA polymerase, a cap analogue, an RNAse inhibitor, Pyrophosphatase, MgCl2, an antioxidant (DTT), betaine, Citrate.

The respective components may be provided by a media supply rack (not shown). The produced IVT master mix is guided from the unit for preparing an IVT master mix 12 via line 121 into the bioreactor 1 according to the present invention. Apart from the IVT master mix, DNA is provided to the bioreactor 1 via feed in line 122. Additionally, the bioreactor 1 may be filled with a wash buffer via feed in line 123. It shall be understood, that filling of the bioreactor 1 processes through the inlet port 8 of the bioreactor 1, which is exemplarily shown in and discussed in context of FIGS. 12-15. With further reference to FIG. 5, a raw RNA product is directed via line 124 to a conditioner 13, e.g. working by tangential flow filtration. Following the conditioning, the RNA is directed to a device for RNA purification 14 (e.g. RP-HPLC, using a method disclosed in WO2008/077592; PureMessenger®). The device for RNA purification 14 is preferably a RP-HPLC device for automated purification and fractionation of the raw RNA. The device for RNA purification 14 may, additionally, or alternatively comprise an oligo dT purification device for automated purification and fractionation of the raw RNA. As indicated by the dotted arrow, the RNA may be subsequently directed to further devices, e.g. another device for RNA conditioning, e.g. by tangential flow filtration, and/or a device for RNA sterile filtration.

As a suitable environment for preforming a process in context of the present invention, a process room or housing may be provided. The process room or housing may be separated from the control systems needed to control and/or monitor the process. In the process room, the experimental set-up may be located. The front of the process room may, for instance, be opened by sliding doors. The base frame of the process room may consist of a modular setup that may be divided into three parts. As an example, the three modules may consist of a one meter module, a two meter module and a backpack with a total length of 3.5 meter and a height of about 2 meter. Further, an exhaust system may be included, which may require additional space. The media supply may be located in the one meter module and shall be physically separated from the actual process room located in the two meter module by a separation wall. A separation wall may, for instance, be realised by a glass divider and also a PVC curtain located behind the sliding doors.

The inner process room may be optionally connected to an exhaust system. It may be desirable, that the liquids which are being processed require further safety measures. This includes explosion protection and/or further biological and chemical safety measures, which may be included in the process room.

Figure 16:
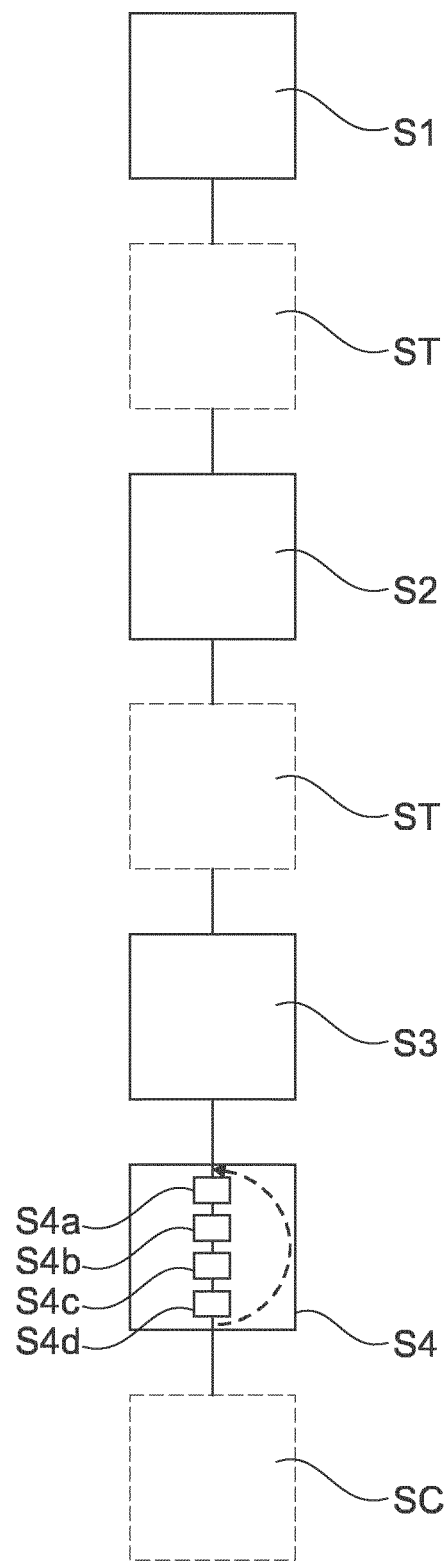
FIG. 16 shows an example of a method for transcribing DNA into RNA according to an embodiment.

FIG. 16 shows a flow diagram for a method for RNA in vitro transcription according to an embodiment of the present invention. The method comprises the step S1, providing magnetic particles, DNA templates, a DNA immobilisation buffer and an IVT master mix in a reaction vessel of a bioreactor according to an embodiment of the present invention. In a step S2 the magnetic particles, the DNA templates and the DNA immobilisation buffer are mixed by means of a cooperation of the magnetic particles and a magnet unit of the bioreactor in order to obtain DNA magnetic particles, which are the DNA templates immobilized on the free-floating magnetic particles. In a method step S3, the DNA magnetic particles are mixed with the IVT master mix by means of a cooperation of the DNA magnetic particles and the magnet unit to obtain RNA. After step S3, the method may comprise step S4, comprising capturing DNA magnetic particles by means of the magnet unit and collecting/harvesting obtained in vitro transcribed RNA e.g. through the outlet port (S4a), providing fresh IVT master mix in a reaction vessel of a bioreactor of the first aspect (S4b), releasing captured DNA magnetic particles to provide free-floating DNA magnetic particles (S4c), mixing the free-floating DNA magnetic particles with the IVT master mix by means of a cooperation of the DNA magnetic particles and the magnet unit to obtain RNA (S4d), and finally removing the DNA magnetic particles from the RNA to obtain DNA free in vitro transcribed RNA. Notably, S4 may be performed several times.

In addition to the above steps, a step ST of tempering the reaction vessel of the bioreactor can be performed between steps S1 and S2 or/and between steps S2 and S3. A cleaning or sanitizing step SC, where the reaction vessel is cleaned with a cleaning fluid and/or cleaning gas, may in addition follow step S3.

Figure 17:
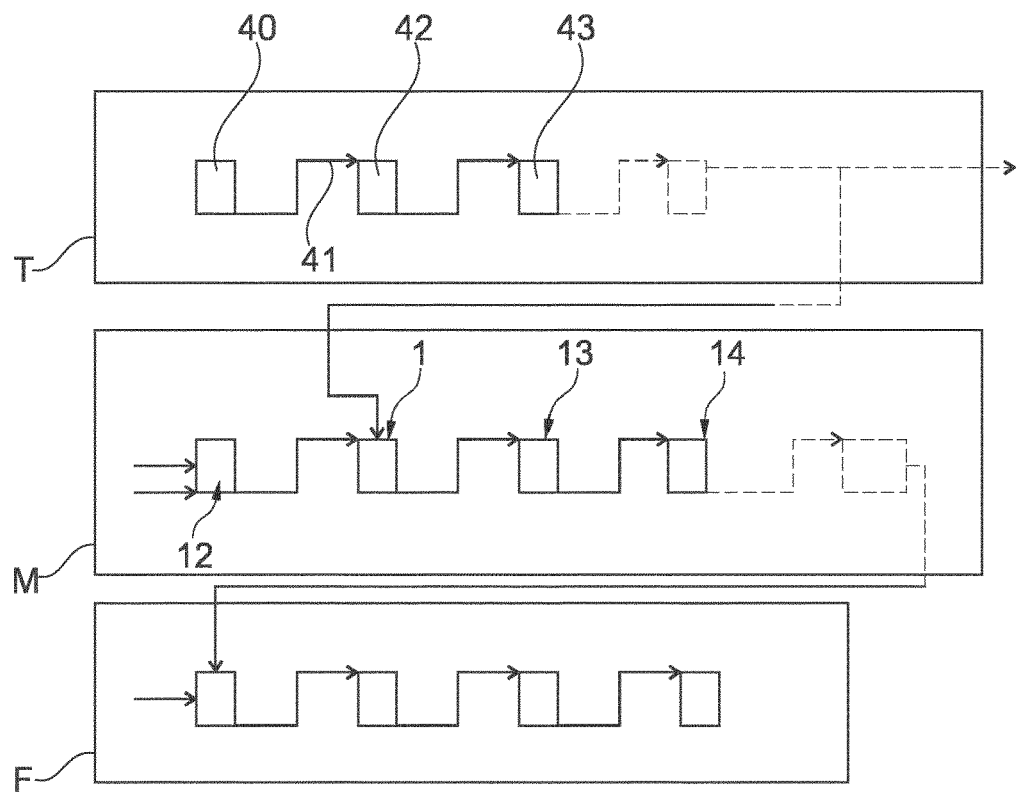
FIG. 17 shows an exemplary apparatus for automated RNA production according to an embodiment.
Figure 18:
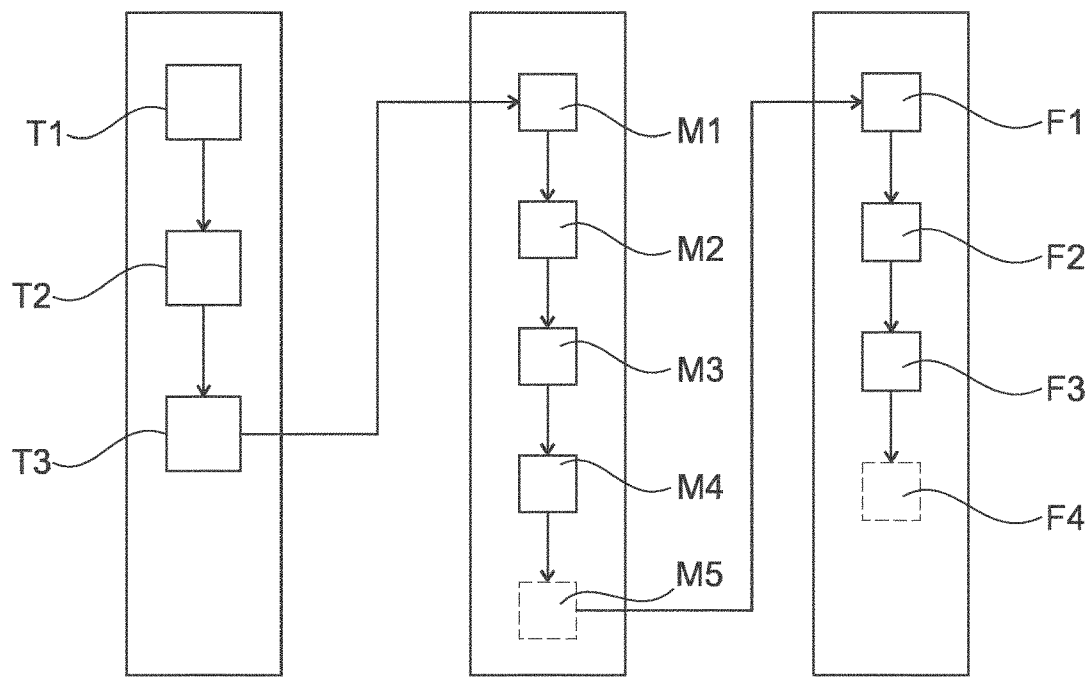
FIG. 18 shows an exemplary process overview for RNA production according to an embodiment.

FIGS. 17 and 18 refer to embodiments of an automated apparatus for RNA manufacturing according to the present invention. In FIG. 17, an example with modules of the automated apparatus and elements for each module is shown. The apparatus comprises a module for DNA synthesis ("template generator"), T, a module for transcribing DNA into RNA, M, and a module for RNA formulation and fill and finish, F. The module for DNA synthesis comprises a pre-mixer 40, which is a unit for preparing PCR master mix 41, which is guided to a unit for preparative PCR 42. The obtained raw DNA template is subsequently guided to a unit for DNA conditioning 43. The dotted line as well as the dotted box indicate, that the conditioned DNA template may be subsequently guided to additional units, such as a unit for purification (e.g. comprising RP-HPLC and/or oligo dT). A purified DNA may then be released as indicated by the dashed arrow pointing horizontally out of module T. However, purified DNA may also be provided to module M, in particular to element 1, a bioreactor, of module N. As an additional input, the bioreactor 1 obtains an IVT master mix from the unit for preparing an IVT master mix 12. The raw RNA obtained by an RNA in vitro transcription reaction within the bioreactor 1 is guided to a unit for conditioning the raw RNA (e.g. comprising a TFF), 13, and subsequently to a unit for RNA purification 14 (e.g. comprising RP-HPLC and/or oligo dT). As indicated by the dotted line and dotted box, additional units may follow that further process and/or refine the obtained RNA (e.g. an RNA capping module for adding a cap0 or cap1 structure to in vitro transcribed RNA, an RNA polyadenylation module, an RNA mixing module, an RNA spray drying module, an RNA lyophilization module). After the described steps, the RNA is provided to module F. In this module, e.g. LNP encapsulated RNA may be produced by a combination of different units comprising at least one of a unit for mixing, a unit for conditioning (e.g. via TFF), a unit for sterile filtration and a unit for filling the obtained drug product.

FIG. 18 shows an overview of method steps comprising DNA synthesis, DNA purification and RNA in vitro transcription as performed in context of Example 1 described below.

EXAMPLE

The following Example is merely illustrative and shall describe the present invention in a further way. The Example shall not be construed to limit the present invention thereto.

Example: Model Batch

As an illustrative example of the processes and methods described in context of the invention, an example model batch process has been performed manually in the laboratory. The respective method steps are depicted in FIG. 18. In course of a first step, a DNA template generation step, the sub steps of a PCR (polymerase chain reaction), T1, and DNA purification (using RP-HPLC), T2, as well as AXP Purification (using Agencourt AMPure XP) have been performed. Thereby, the last sub step T3 shall not be performed in the final and automated process according to embodiments of the present invention and is only required for a manually processed model batch as in the Example. In a next step, RNA in vitro transcription is performed, wherein this step comprises the following sub steps: as a first sub step DNA immobilisation, M1, wherein the DNA templates are immobilised on free-floating magnetic beads. The second sub step M2 refers to the RNA in vitro transcription reaction. As a next sub step (not indicated in FIG. 20), AXP purification is performed, wherein again, this purification step shall not be performed in the final and automated process, but is performed only in the manually processed model batch. In sub step M3, the produced raw RNA is purified. Sub step M4 refers to Ultrafiltration (UF)/diafiltration (DF) e.g. using TFF, and as sub step M5, sterile filtration is performed. The example is non-limiting, and to highlight the fact, that additional method steps may be performed, the dashed box with reference sign M5 indicates that there may be additional sub steps within the RNA in vitro transcription step. As third step, formulation is performed on the produced raw RNA. To this end, in-line mixing was carried out in sub step F1. As a next step not indicated in the FIG. 20, a dialysis was carried out, wherein also this sub step is intended to be left out in case of the final and automated process and was only required for the manually processed model batch. The next sub step F2 refers to UF/DF, followed by a cryoprotection step also not indicated on FIG. 20, as this step is only required for the manually processed model batch. The last three sub steps may also be combined in a single UF/DF step. In sub step F3, a sterile filtration is performed. The dashed box with reference sign F4 indicates that additional sub steps may be incorporated into a method according to the invention. In case of the Example, however, no further sub steps were performed.

A repeated batch RNA in vitro transcription as performed within the Example comprises the steps of PCR template generation and DNA template purification, both performed in a template generator. Within the next step of RNA production, in a first sub step template immobilisation takes place, followed by a repeated batch RNA in vitro transcription reaction step. The latter is then followed by a repeated batch HPLC sub step and finally a single batch TFF sub step.

Figure 19:
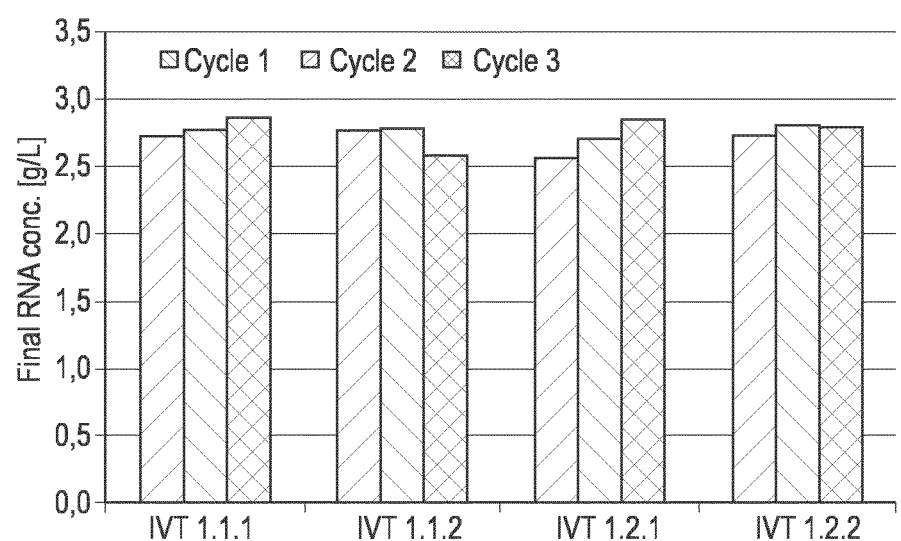
FIG. 19 show the result of a repeated batch RNA in vitro transcription using the same immobilized DNA template over 3 IVT reactions. The experiment was performed as described in Example 1.

Results on the recycled, i.e. repeated RNA in vitro transcription reaction are collected in FIG. 19. The same immobilized DNA template was used over 3 RNA in vitro transcription reactions. The results show a stable performance over the three cycles of RNA in vitro transcriptions, both quantitatively and qualitatively.

Figure 20A:
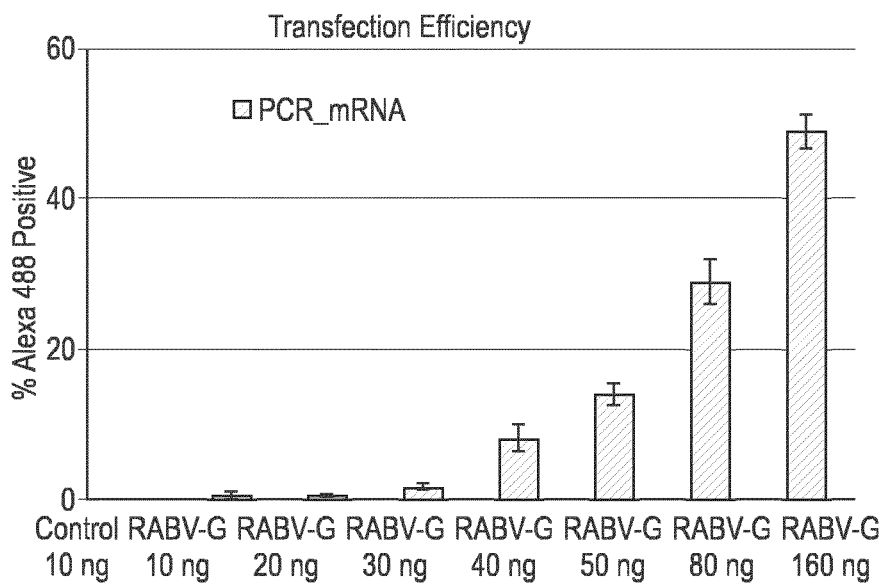
FIGS. 20A, B shows the potency on the produced RNA expressed in HepG2 cells (RAVG mRNA). The experiment was performed as described in Example 1.
Figure 20B:
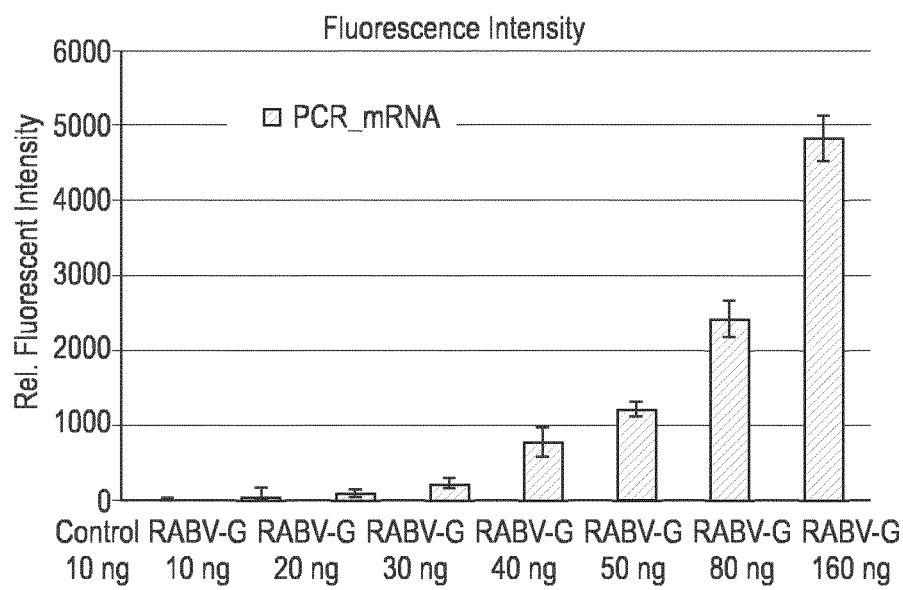

In FIGS. 20A and B, an RNA potency assay of the produced drug substance, the produced (HPLC purified) RNA, expressed in HepG2 cells (RAVG mRNA) is shown, demonstrating that the repeated RNA in vitro transcription reaction that may be suitably performed in the bioreactor of the invention produces RNA of high quality in a robust and reliable manner.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

LIST OF REFERENCES SIGNS 1 bioreactor
10 support
11 horizontal bar
110 arrow
111 arrow
2 reaction vessel
21 inner surface of the reaction vessel
23/outer surface of the reaction vessel
24 flow breaker
25 first leg of the reaction vessel
251 first conduit
26 second leg of the reaction vessel
261 second conduit
27 filling level
28 maximal fluid amplitude
3 magnet unit
31 magnetic ring
32 rod
320 first rod
321 free end of the first rod
322 second rod
323 free end of the second rod
33 centre of the magnet unit
34 inner circumference of the magnetic ring
350 guide plate
351 electric coil
352 cooling means
36 spindle axis
37 arm
38 rotation driving means
39 driving means
361 movable support
362 arrow
363 arrow
5 temperature element
51 heat exchange channel
52 first end heat exchange channel
53 second end heat exchange channel
54 heating wire
55 heat isolation material
6 medium port/outlet port
60 valve means
61 magnetic trap
62 multi position valve
63 hall sensor
64 flow cells
65 arrow
66 medium pipe/outlet pipe
67 waste channel
7 exit port/waste port
71 multi position valve
72 waste flow cell
73 exhaust duct
74 waste channel
76 pressure sensor
8 inlet port
81 heating
83 inlet pipe
91 temperature sensor
92 additional sensor
12 IVT master mix
121 line into the bioreactor
122 line
123 line
124 line 13 conditioner
14 RNA purification
40 pre-mixer
41 PCR master mix
42 preparative PCR
43 unit for DNA conditioning

The invention claimed is:

1. A bioreactor (1) for RNA in vitro transcription comprising:
   (a) a reaction vessel (2) comprising magnetic particles, DNA templates, a DNA immobilization buffer, DNA magnetic particles and an in vitro transcription (IVT) master mix, said IVT master mix comprising ribonucleoside triphosphates and DNA dependent RNA polymerase,
      wherein the DNA magnetic particles are DNA templates immobilized on the magnetic particles, and
   (b) a magnet unit (3) positioned at the reaction vessel,
      wherein the magnet unit is configured to capture or to introduce a movement of the magnetic particles and the DNA magnetic particles,
      wherein the magnet unit (3) comprises a magnetic ring (31), and wherein the magnetic ring (31) is designed to surround the reaction vessel (2), wherein:
      the magnet unit (3) is a permanent magnet or an electromagnet movable in a longitudinal direction (362) along a longitudinal axis of the reaction vessel (2) and/or a transversal direction (363) towards and apart from the reaction vessel (2);
      the magnet unit (3) is configured to rotate around the longitudinal axis of the reaction vessel (2), and wherein a rotation direction of the magnet unit (3) is switchable during mixing; and
      the magnet unit (3) further comprises a first driving means (36) configured to rotate the magnetic ring (31) and a second driving means (37) configured to move the magnetic ring (31) in the vertical direction.

2. The bioreactor (1) according to claim 1, wherein an inner surface of the reaction vessel (2) has an ellipsoid, an oval inner geometry or an egg-shape inner geometry.

3. The bioreactor (1) according to claim 1, wherein an inner surface of the reaction vessel (2) has a shape without edges.

4. The bioreactor (1) according to claim 1, wherein the movement of the magnetic particles and the DNA magnetic particles is configured to avoid sedimentation of the particles and to keep the magnetic particles free-floating.

5. The bioreactor (1) according to claim 1, wherein the magnet unit (3) is an array of electromagnets positioned on or in proximity to an outer surface of the reaction vessel.

6. The bioreactor (1) according to claim 1, wherein the magnet unit (3) is an electromagnet and at least an induction coil or a pair of Helmholtz coils movable in a longitudinal direction (110) along a longitudinal axis of the reaction vessel (2) and rotatable (111) around a vertical axis of the reaction vessel (2).

7. The bioreactor (1) according to claim 1, wherein the magnetic ring (31) comprises at least a first rod (320) and a second rod (322) extending from an inner circumference (34) of the magnetic ring (31) to a centre (33) of the magnetic ring (31), so that free ends (321, 323) of the first and second rod (320, 322) face each other.

8. The bioreactor (1) according to claim 7, wherein the free end (321) of first rod (320) comprises a magnet with an N pole and the free end (323) of the second rod (322) comprises a magnet with an S pole.

9. The bioreactor (1) according to claim 1, wherein the magnetic ring (31) comprises a plurality of rods (320, 322), wherein the plurality of the rods (320, 322) extend from an inner circumference (34) of the magnetic ring (31) to a centre (33) of the magnetic ring (31) and are arranged in a star shape evenly spaced apart from each other, and wherein a magnet with an N pole and a magnet with an S pole are arranged alternately at a free end of each rod.

10. The bioreactor (1) according to claim 9, wherein the magnetic ring (31) and the rods (320, 322) are configured to form a laminated stack for shielding periphery components from a magnet field.

11. The bioreactor (1) according to claim 1, wherein the magnetic ring (31) comprises a plurality of guide plates (350) extending from an inner circumference (34) of the magnetic ring (31) to a centre of the magnetic ring (31), and wherein each guide plate (350) comprises an electric coil (351) configured for generating a magnetic field.

12. The bioreactor (1) according to claim 1, wherein the magnetic ring (31) is arranged in a housing (352) having cooling means.

13. The bioreactor (1) according to claim 1, wherein a temperature element (5) is positioned between an inner surface (21) and an outer surface (23) of the reaction vessel (2) for adjusting a temperature of the reaction vessel (2), and wherein the temperature element (5) comprises a heat exchange channel (51) at least partially helically surrounding the reaction vessel (2) in a radial direction of the reaction vessel (2).

* * * * *